(12) United States Patent
Atzler et al.

(10) Patent No.: US 9,347,882 B2
(45) Date of Patent: May 24, 2016

(54) DYNAMIC SIGNAL EXTENSION IN OPTICAL DETECTION SYSTEMS

(71) Applicant: Molecular Devices, LLC, Sunnyvale, CA (US)

(72) Inventors: Josef J. Atzler, Hallein (AT); Bernhard Schinwald, Munderfing (AT)

(73) Assignee: Molecular Devices, LLC, Sunnyvale, CA (US)

( * ) Notice: Subject to any disclaimer, the term of this patent is extended or adjusted under 35 U.S.C. 154(b) by 564 days.

(21) Appl. No.: 13/737,279

(22) Filed: Jan. 9, 2013

(65) Prior Publication Data

US 2013/0119277 A1    May 16, 2013

Related U.S. Application Data

(63) Continuation-in-part of application No. 13/166,595, filed on Jun. 22, 2011, now Pat. No. 8,496,879.

(51) Int. Cl.
*G01N 21/76*   (2006.01)
*G01N 21/64*   (2006.01)
(Continued)

(52) U.S. Cl.
CPC . *G01N 21/64* (2013.01); *G01J 3/02* (2013.01); *G01J 3/021* (2013.01); *G01J 3/0202* (2013.01); *G01J 3/0218* (2013.01); *G01J 3/0232* (2013.01); *G01J 3/0235* (2013.01); *G01J 3/0256* (2013.01); *G01J 3/0291* (2013.01); *G01J 3/10* (2013.01); *G01J 3/427* (2013.01); *G01J 3/4406* (2013.01); *G01N 21/645* (2013.01); *G01N 21/6428* (2013.01); *G01N 21/763* (2013.01);

(Continued)

(58) Field of Classification Search
CPC . G01N 21/47; G01N 21/474; G01N 21/8806; G01N 2201/0612; G01N 2201/105; G01N 21/6428; G01N 21/6452; G01N 21/65; G01N 2021/6419; G01N 2021/6421; G01N 21/645; G01N 2021/6484; G01N 21/64
See application file for complete search history.

(56) References Cited

U.S. PATENT DOCUMENTS 4,158,505 A * 6/1979 Mathisen .................. G01J 3/02
356/308
5,347,122 A * 9/1994 Ansorge et al. .......... 250/227.11
(Continued)

OTHER PUBLICATIONS

"2 Tutorial on Fluorescence and Fluorescent Instrumentation", pp. 1-12, no date; http://fmrc.pulmcc.washington.edu/DOCUMENTS/FMRC299.pdf.*

(Continued)

*Primary Examiner* — Yelena G Gakh
(74) *Attorney, Agent, or Firm* — Bella Fishman

(57) ABSTRACT

Systems and methods for measuring a target in a sample, the target being capable of generating an emitted light in response to an excitation light. In an example system, an excitation light source generates the excitation light along an excitation optical path. An attenuation filter arrangement selectively adds an attenuation filter to the excitation optical path. The attenuation filter attenuates the excitation light by a corresponding attenuation factor. The excitation light exits the attenuation filter arrangement along the excitation optical path to illuminate the sample. A light energy detector receives the emitted light generated in response to the excitation light, and outputs a measured signal level corresponding to an emitted light level. If the light energy detector indicates an overflow, signal measurement is repeated with attenuation filters of increasing attenuation factors until the measured signal level does not overflow.

13 Claims, 26 Drawing Sheets

(51) Int. Cl.
*G01J 3/02* (2006.01)
*G01J 3/10* (2006.01)
*G01J 3/427* (2006.01)
*G01J 3/44* (2006.01)
*G01N 21/17* (2006.01)

(52) U.S. Cl.
CPC ........ *G01N21/6408* (2013.01); *G01N 21/6445* (2013.01); *G01N 2021/1738* (2013.01); *G01N 2021/6415* (2013.01); *G01N 2021/6419* (2013.01); *G01N 2021/6441* (2013.01); *G01N 2021/6482* (2013.01); *G01N 2201/024* (2013.01); *G01N 2201/062* (2013.01); *G01N 2201/0618* (2013.01); *G01N 2201/0621* (2013.01); *G01N 2201/0692* (2013.01); *G01N 2201/0696* (2013.01)

(56) References Cited

U.S. PATENT DOCUMENTS

| 5,606,170 | A | * | 2/1997 | Saaski et al. | 250/458.1 |
| 6,075,613 | A | * | 6/2000 | Schermer et al. | 356/446 |
| 6,503,711 | B1 | * | 1/2003 | Krull et al. | 506/17 |
| 8,389,957 | B2 | * | 3/2013 | Jaffe | G01N 21/6408 250/216 |

OTHER PUBLICATIONS

Bürck "SPME in Near-IR Fiber-optic Evanescent Filed Absorption Spectroscopy: A Method for Rapid, Remote in situ Monitoring of Nonpolar Organic Compounds in Water", Chapter 26, in "Applications of Solid Phase Microexctraction", ed. Pawliszyn, 1999, pp. 638, 642, 643.*

* cited by examiner

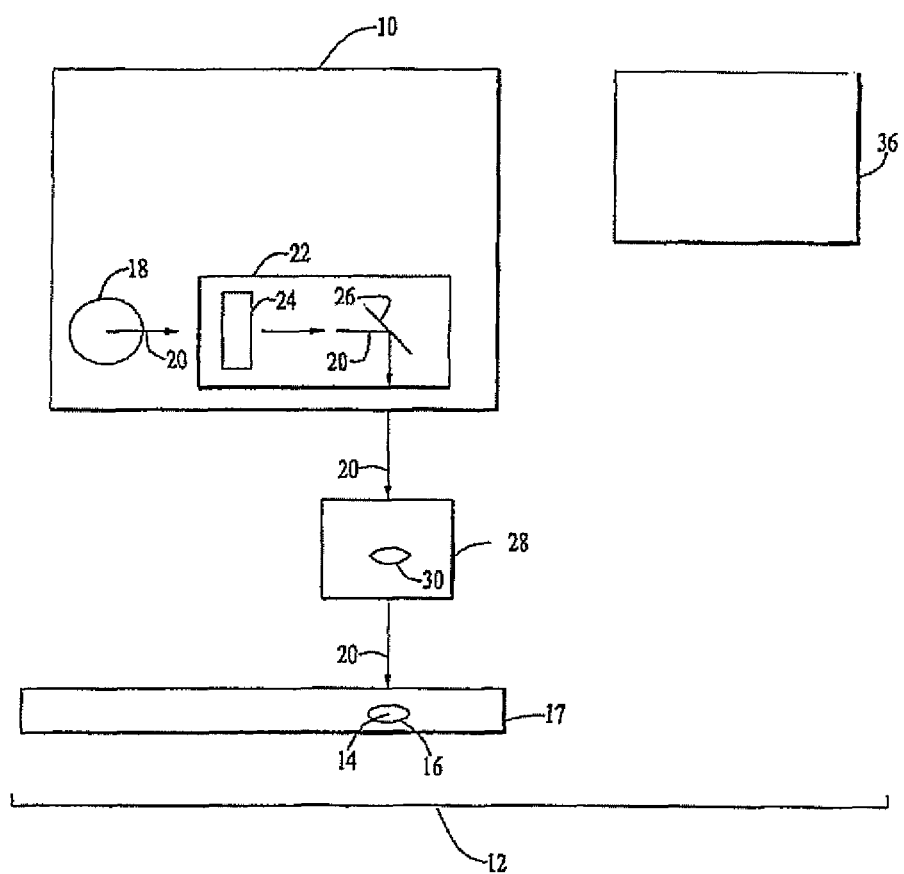

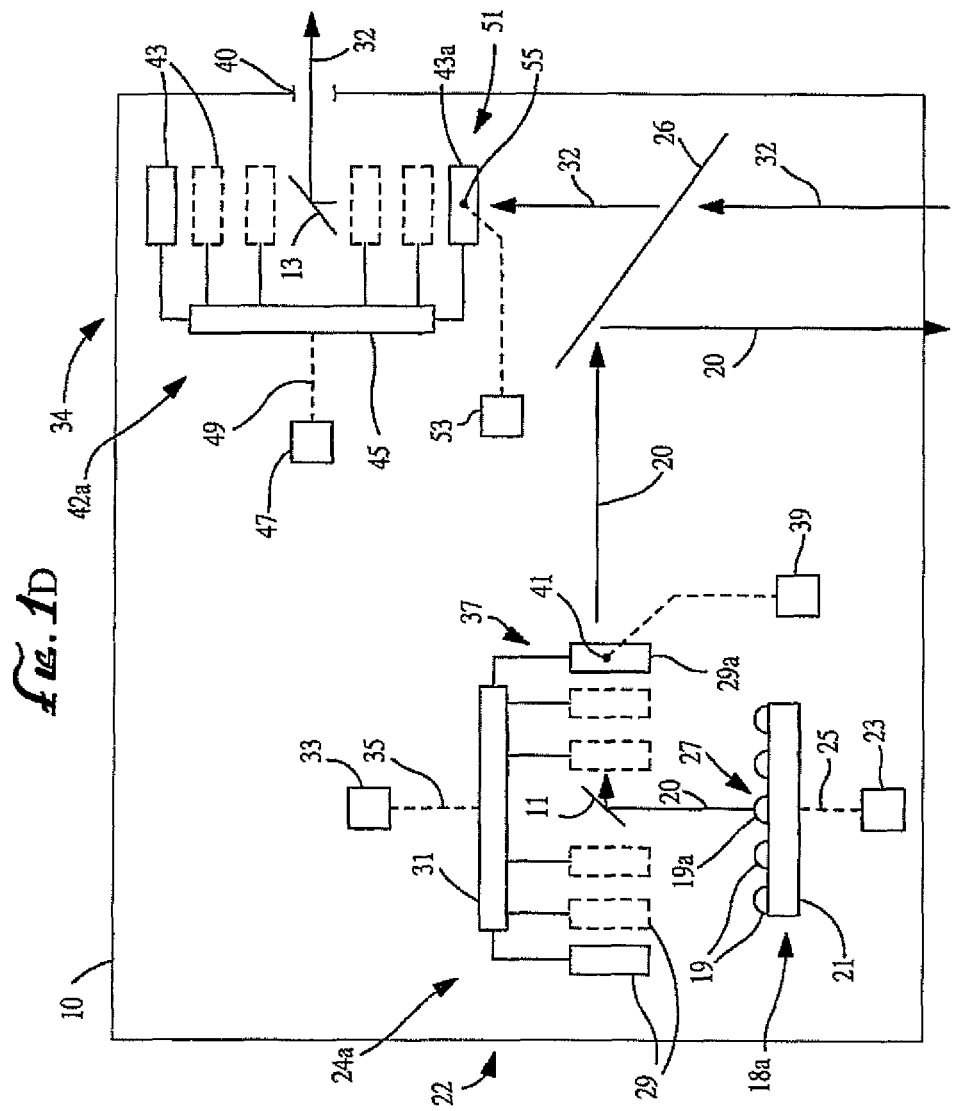

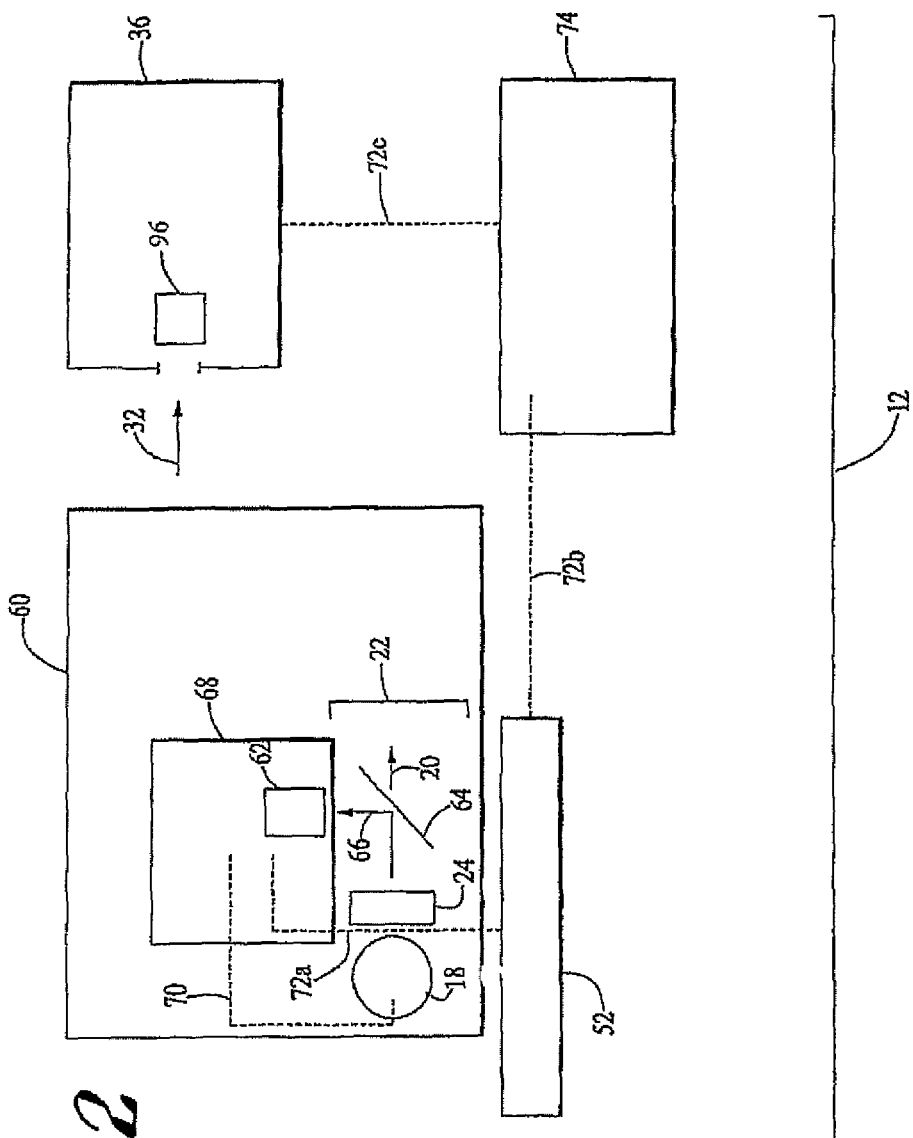

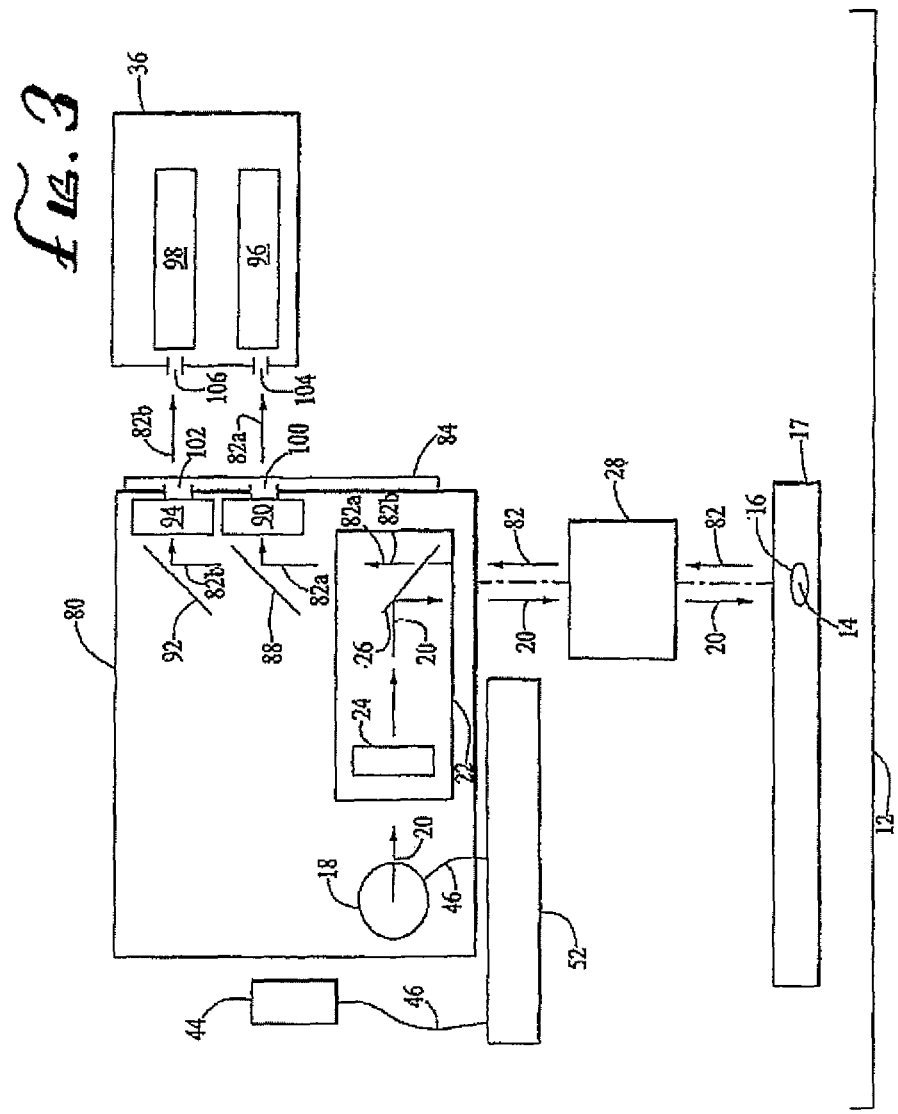

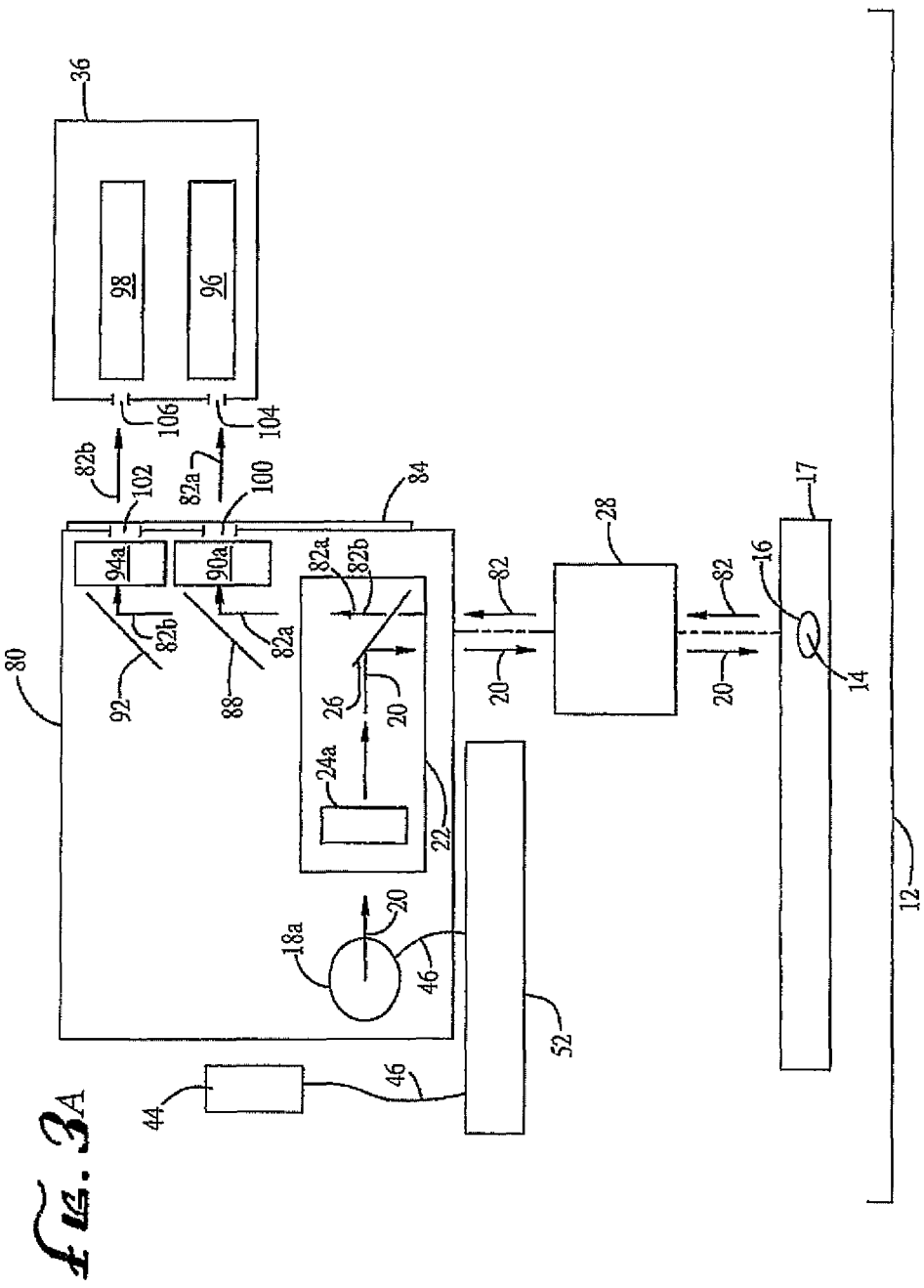

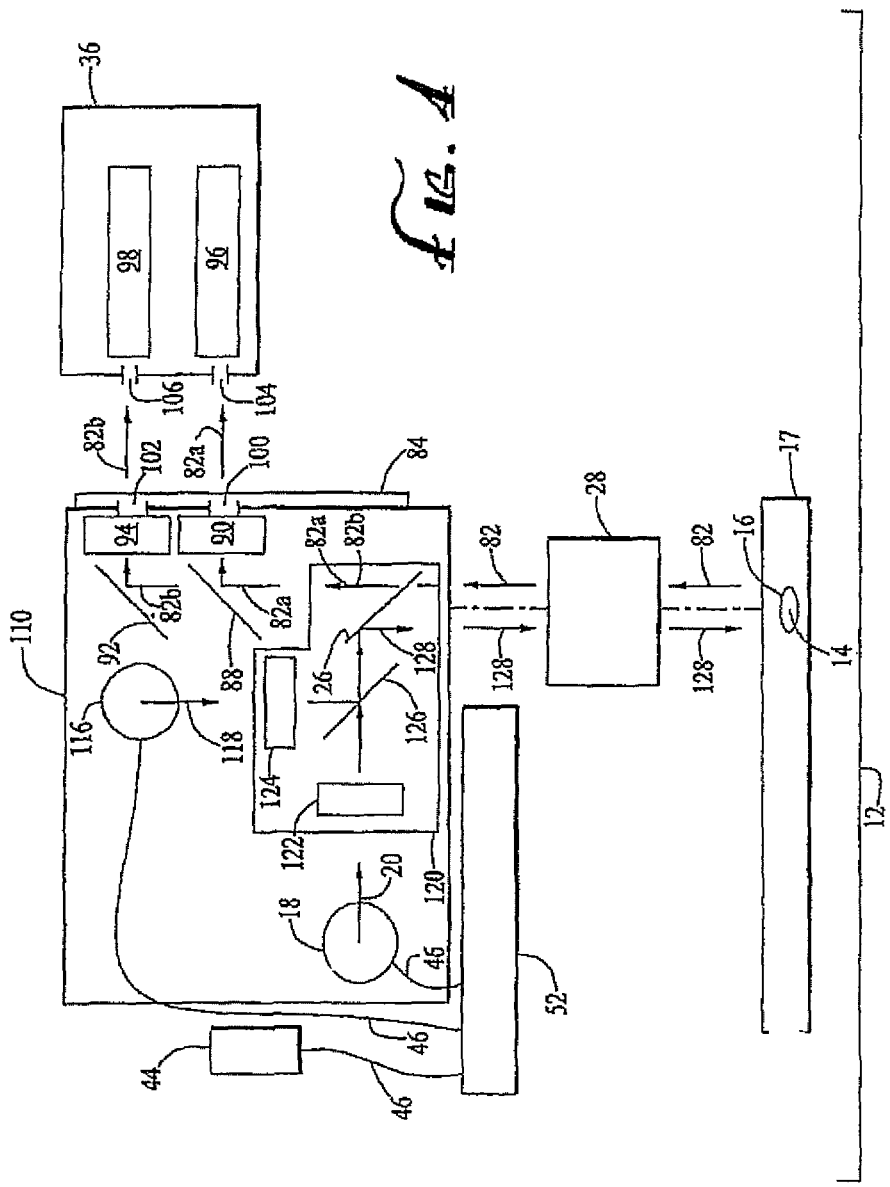

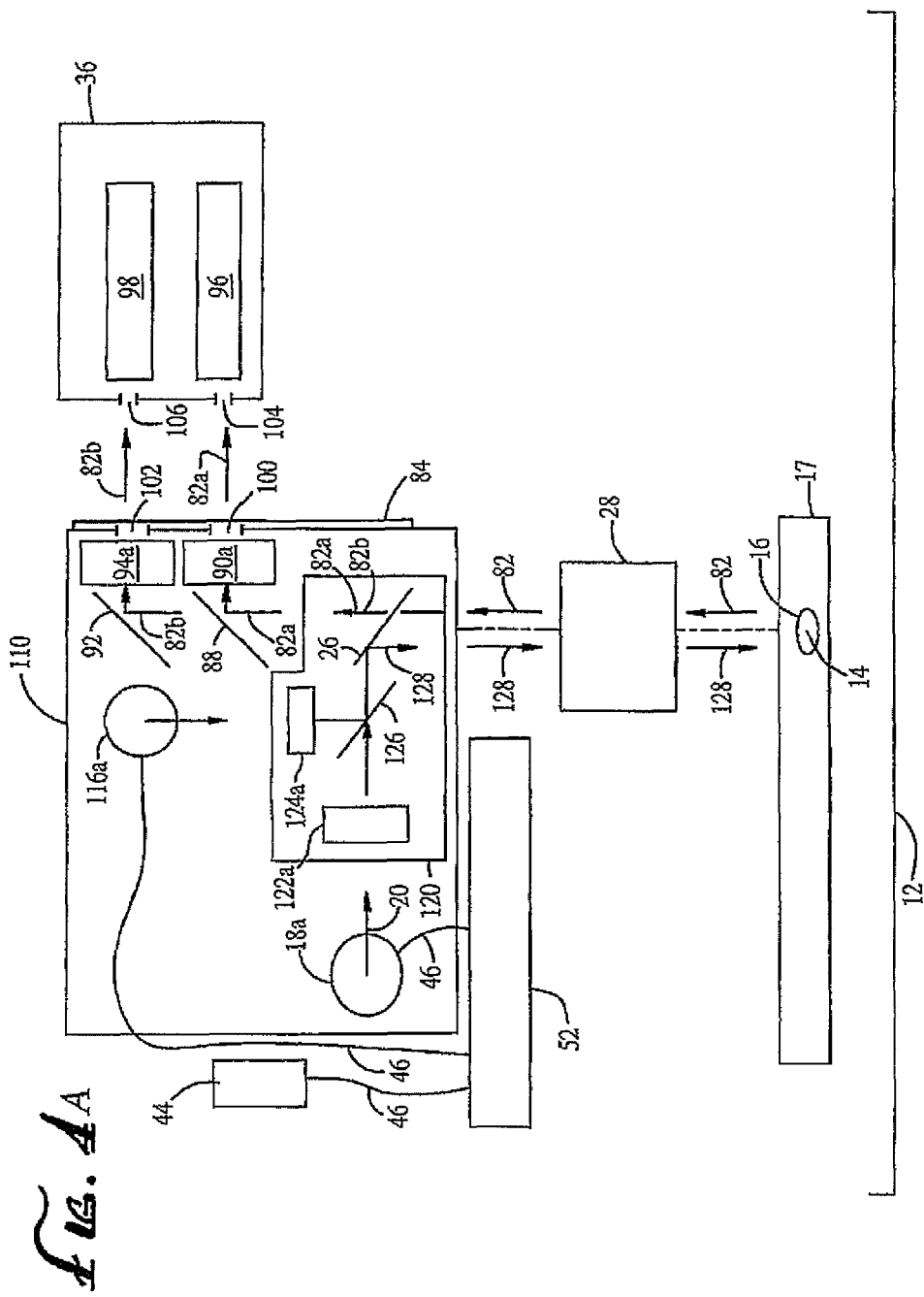

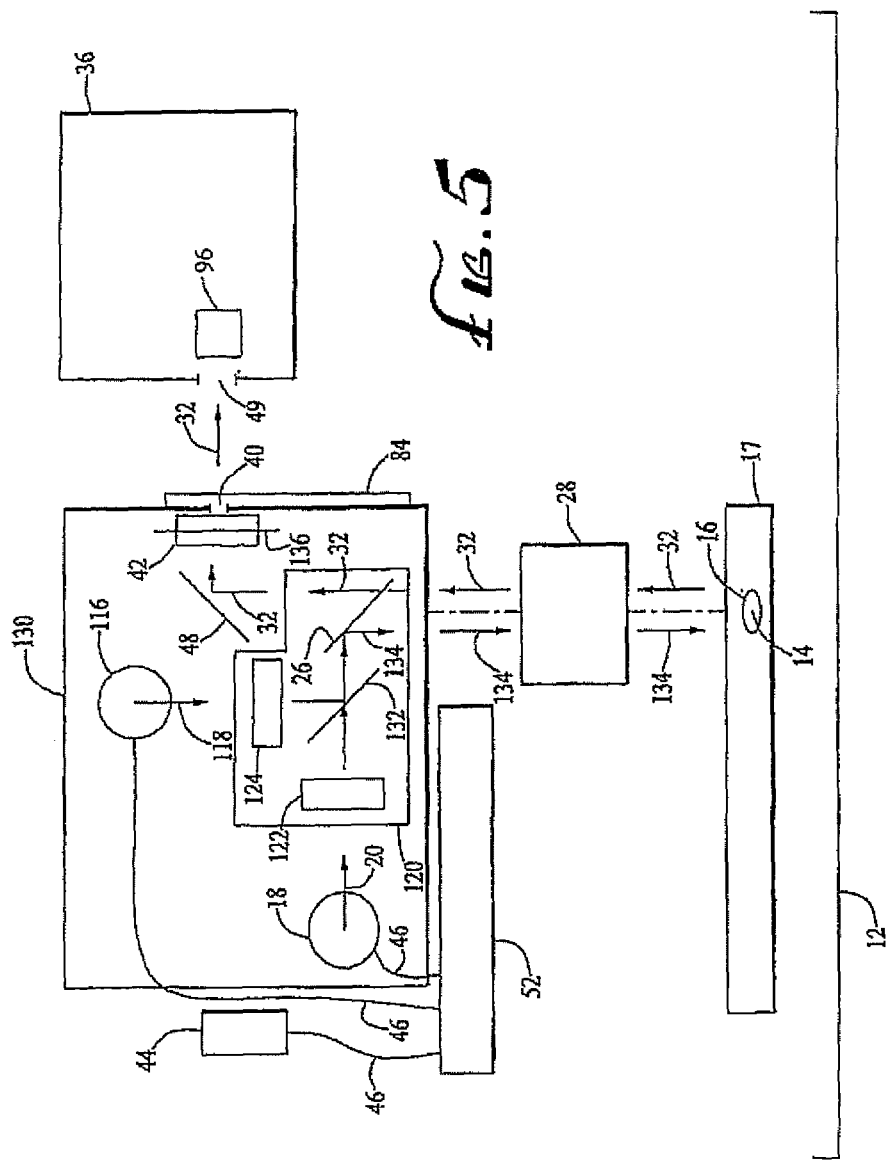

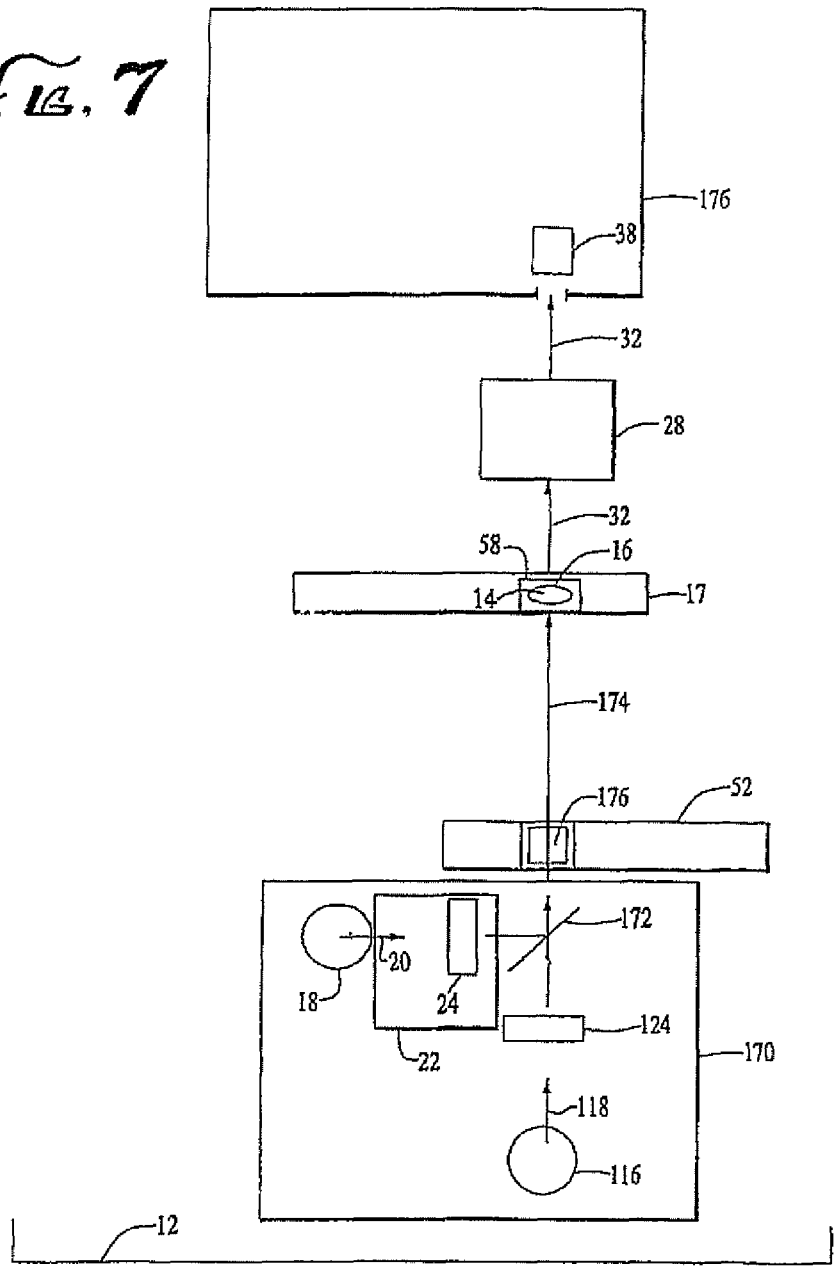

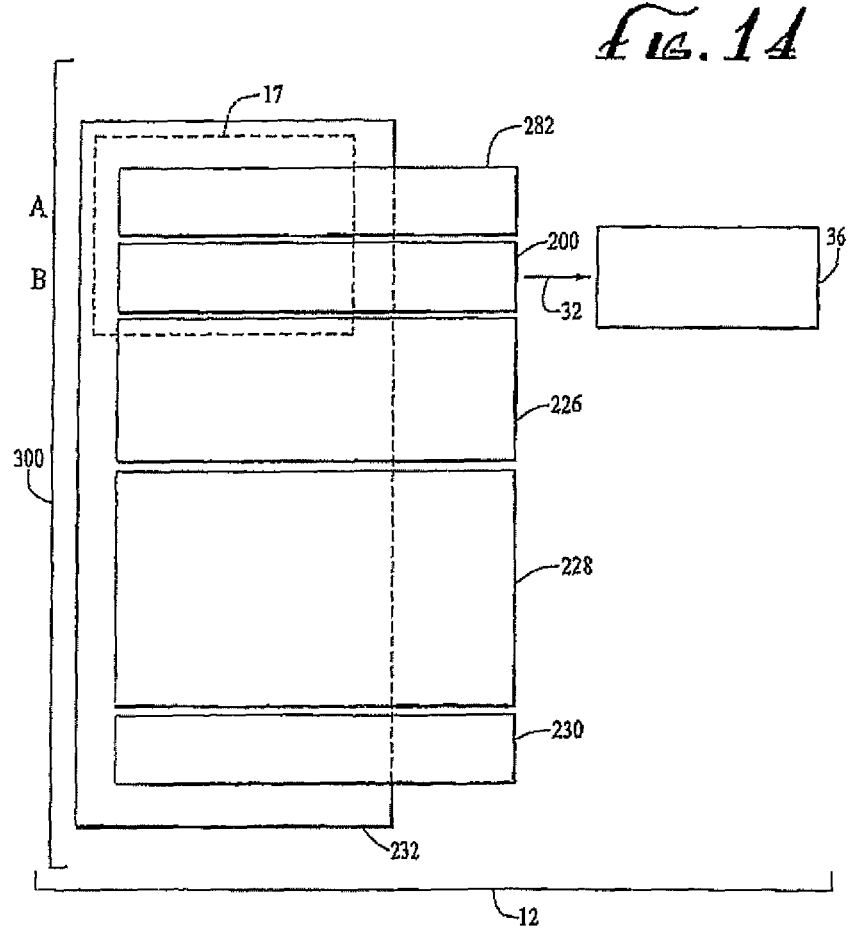

DYNAMIC SIGNAL EXTENSION IN OPTICAL DETECTION SYSTEMS

RELATED APPLICATIONS

This application is a continuation-in-part of co-pending U.S. patent application Ser. No. 13/166,595, filed on Jun. 22, 2011, and titled "OPTICAL DETECTION UTILIZING CARTRIDGE WITH TUNABLE FILTER ASSEMBLY," the content of which is incorporated by reference herein in its entirety.

TECHNICAL FIELD

This present invention generally relates to analytical instruments and methods related to such instruments, and more particularly, to the implementation of dynamic signal extension in such instruments.

BACKGROUND

Multimode analytical instruments, also referred to as multimode readers, are apparatus that can perform multiple analytical assays in a single instrument. Standard multimode readers, used within the life science industry, can measure the most common types of assays (i.e., applications, such as fluorescence, luminescence, and absorbance) in a single instrument. The use of a single instrument to perform these assays is advantageous over using multiple dedicated instruments to perform the same measurements. This lies in the fact that a multimode reader can provide ease of use, a better price performance ratio, and require less bench top area than multiple instruments.

Generally, these instruments have built-in general purpose (i.e., white) light sources, such as halogen lamps and xenon flash lamps, and general purpose detectors such as photomultiplier tubes (PMTs) and silicon photodiodes. The instruments also typically include optical filters mounted into wheels or slides, and application specific beamsplitters installed into slides, or into revolver like mechanisms. Multimode readers may also combine filter-based and monochromator-based technology. While components are configured to perform a variety of types of assays, expanding the multimode reader to perform new assays and new applications was often difficult. From a hardware point of view, specific applications may involve accessing a multitude of driven stages for selecting the correct combination and adjustment of filters, beamsplitters, apertures, and lightguides, for example. In these devices, enabling new applications of a given technology required retrofitting specific optical filters and beamsplitters. Adding new applications often required substantial redesign.

In some example implementations, standardized cartridges having a standard form and shape may be configured with components arranged for specific applications, or types of applications. Such cartridges substantially reduce the amount of redesign and retrofitting involved in adding applications. However, with the exception of applications that employ absorbance-based measurements, the advantages have largely been realized for filter-based technologies.

It would be desirable for a multimode reader to fully use both filter-based and monochromator-based technologies. Such a multimode reader would be capable of using a PMT in the photon counting mode and of performing dynamic extension via light level control of the source light (i.e. the LEDs). Such a reader would also be capable of measurements in the analog mode where a Xenon flash lamp light source is used in combination with a monochromator. The flash duration involved with a Xenon flash lamp is typically in the single micro second range. This range of flash duration is too short to permit the use of photon counting for a measurement.

One way to perform dynamic signal extension with a PMT in analog mode is to control the signal output of the source light, which is, as an example, a Xenon flash lamp. Control of the Xenon flash lamp output is difficult, but the main problem with this solution is that it would require a change to the hardware. The control over the output signal level of the PMT may also require discharge capacitors at substantially high power levels. Switching to different levels may not be sufficiently fast enough to address the too short flash duration.

Dynamic extension may also be achieved by varying the gain level of the PMT. In applications that use a flash lamp in combination with a monochromator, the gain level of the PMT cannot be changed quickly enough for the one or several microsecond flash duration. In addition, the gain level of the PMT is not a linear attribute of a PMT. This makes the change of the gain difficult to factor into the result.

The dynamic range of a PMT in analog mode with a constant gain setting is relatively limited to a range of about 5 logs or less. This is too small in some applications where a dynamic range of several times more than 5 logs is needed. Some form of dynamic extension is needed to measure over the full range of the applications.

There is a need in the art for an analytical system that permits variably fast adjustment of the light source output and of the dynamic range of the signal measurement.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a system is provided for measuring a target in a sample, the target being capable of generating an emitted light in response to an excitation light. In an example system, an excitation light source is configured to generate the excitation light along an excitation optical path. An attenuation filter arrangement is configured to selectively add an attenuation filter to the excitation optical path. The attenuation filter attenuates the excitation light by a corresponding attenuation factor. The excitation light exits the attenuation filter arrangement along the excitation optical path to illuminate the sample. A light energy detector receives the emitted light generated in response to the excitation light, measures an emitted light level, and outputs a measured signal level up to a maximum detector level. A controller receives the measured signal level and executes a signal measurement function under program control. The signal measurement function adds the attenuation filter to attenuate the excitation light if the measured signal level indicates an overflow condition in which the measured signal level is greater than the maximum detector level, receives another measured signal level in response to an attenuated excitation light, and processes the measured signal level as a sample measurement value when the measured signal level does not indicate an overflow condition.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can, be better understood by referring to the following figures. The components in the figures are not necessarily to scale, emphasis instead being placed upon illustrating the principles of the invention. In the figures, like reference numerals designate corresponding parts throughout the different views.

FIG. 1A is a schematic view illustrating components of a cartridge according to an embodiment of the present invention.

FIG. 1D is a schematic view of an example of a wavelength-tunable cartridge, according to another embodiment of the present disclosure.

FIG. 2 is a schematic view of a cartridge having source intensity monitoring components according to an embodiment of the present invention.

FIG. 3 is a schematic view of a dual emission cartridge according to an embodiment of the present invention.

FIG. 3A is a schematic view of an example of a dual emission cartridge provided with wavelength-tuning features, according to another embodiment of the present disclosure.

FIG. 4 is a schematic view of a dual emission dual excitation cartridge according to an embodiment of the present invention.

FIG. 4A is a schematic view of an example of a dual emission, dual excitation cartridge provided with wavelength-tuning features, according to another embodiment of the present disclosure.

FIG. 5 is a schematic view of a dual excitation cartridge according to an embodiment of the present invention.

FIG. 7 is a schematic view of a dual wavelength absorbance cartridge according to an embodiment of the present invention.

FIG. 14 is a schematic top view of flash luminescence cartridge system according to an embodiment of the present invention.

DETAILED DESCRIPTION

According to the present invention, a cartridge for use in an apparatus for analyzing a sample is provided. The cartridge has one or more light sources, as well as optical systems and other components, which are specific for a certain type of application such as fluorescence or absorbance. The light source, optical systems, and other components for a specific application are housed in a single cartridge. The cartridge is removably engaged with the apparatus in a "plug-in" format such that the apparatus can be upgraded by substitution or installation of a cartridge, i.e., a new application can be installed by adding or substituting a new cartridge in the apparatus, or an installed cartridge can be substituted with another cartridge of the same purpose which incorporates the latest advancements in technology. The new cartridge may have its components preadjusted and pretested and the cartridge may be automatically identifiable by the apparatus such that the instrument control software can identify an individual cartridge and recognize any application specific parameters stored in the cartridge. Thus, instead of selecting a combination of light sources, optics, and other components for a new application, running a new application is reduced to selecting a single component, i.e., the cartridge, with its interior components preadjusted and pretested, and installing the cartridge in the apparatus. An advantage of the cartridge concept is that an instrument can be upgraded in the field by the user himself—without needing the assistance of a service engineer.

The apparatus may have general purpose detectors (like photomultipliers and photodiodes), which are shared by multiple cartridges, and all applications of the same technology may share certain read heads that interface with the samples to be measured.

Also provided is a wavelength-tunable cartridge in which the wavelength or wavelength band of the excitation path and/or the emission path is tunable.

Figure 1B:
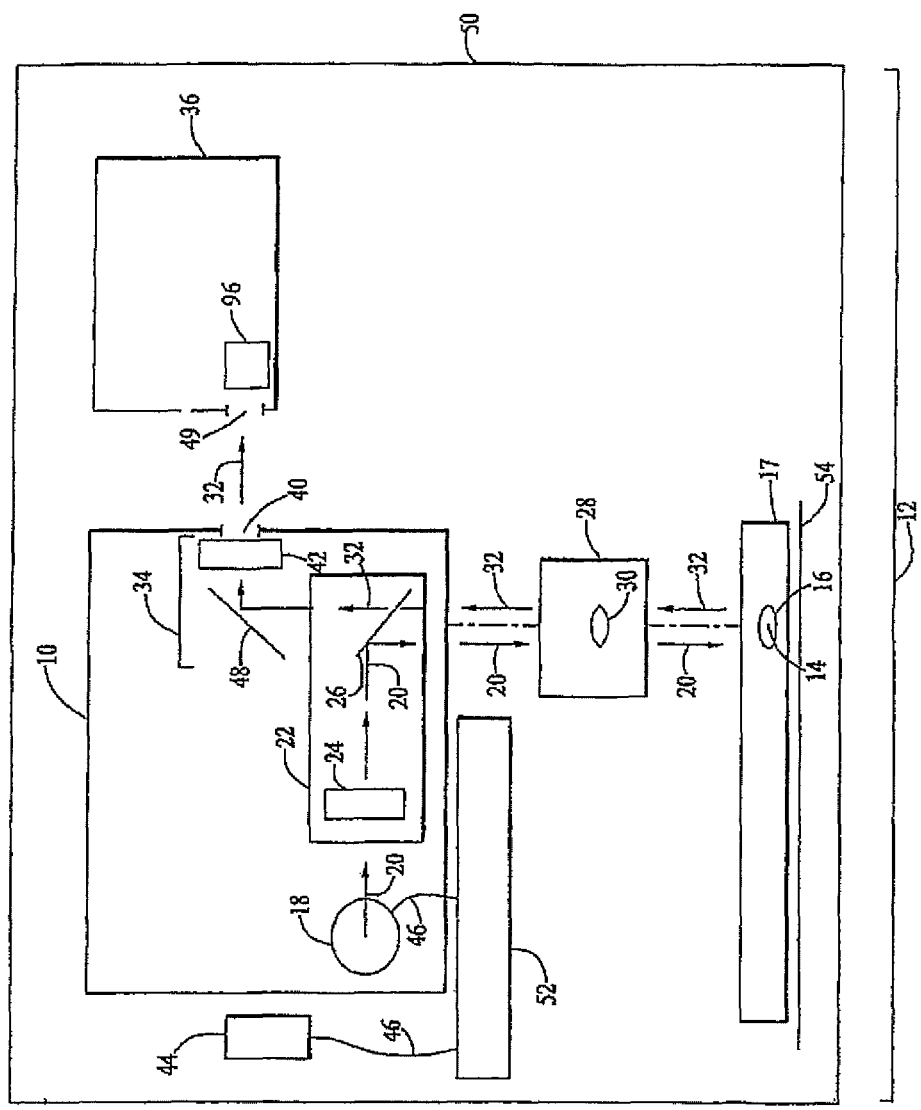
FIG. 1B is a schematic view illustrating components of a cartridge used for a fluorescence application according to an embodiment of the present invention.
Figure 1C:
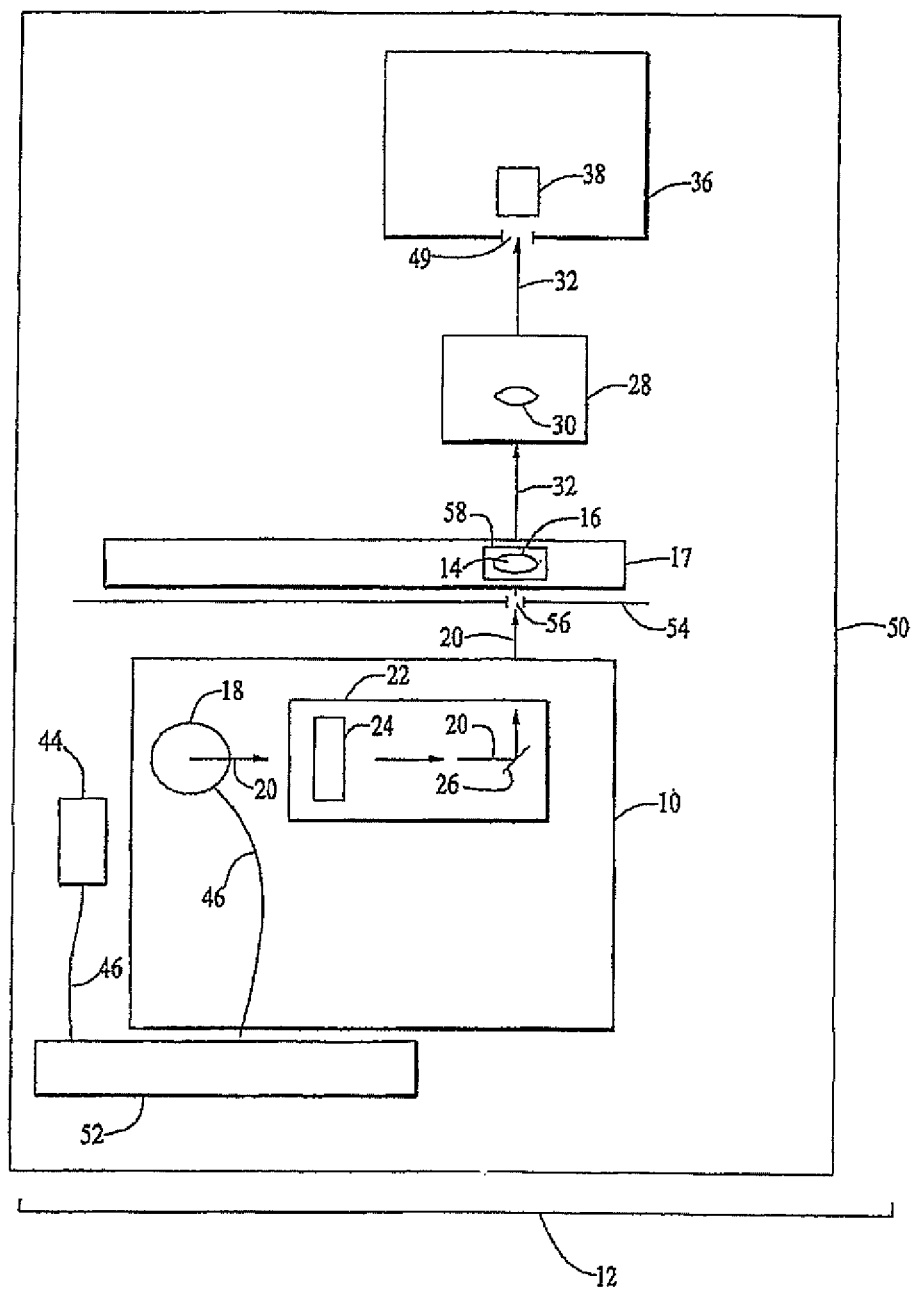
FIG. 1C is a schematic view illustrating components of a cartridge used for an absorbance application according to an embodiment of the present invention.

Referring now to FIGS. 1A, 1B, and 1C a cartridge 10 for use in an apparatus 12 for analyzing a target 14 in a sample 16 is shown. The sample 16 may be held within the apparatus 12 on a sample support 17, such as a microplate. As shown in FIG. 1, the cartridge 10 comprises one or more light sources 18 that separately or in combination produce an exciting light 20. The cartridge 10 is designed to be removably engaged with the apparatus 12. The cartridge 10 has a first optical system 22 which has components for directing the exciting light 20 to the sample 16. The light source 18, such as a light emitting diode (LED) or a laser diode (LD), is collimated by lenses and apertures to emit a collimated beam of light. The first optical system 22 then transmits the exciting light 20 through filters 24, such as a bandpass filter, and then reflects the exciting light 20 out of the cartridge 10 with the help of a reflector 26, such as a dichroic beamsplitter, to a read head 28. The read head 28 directs the exciting light 20 toward the sample 16. The read head 28 contains an objective lens 30 that can be moved up and down. The objective lens 30 focuses the exciting light 20 onto the sample 16. The sample 16, containing the target 14, then produces an emitting light 32 (or emitted light 32), which is directed to a detector 36, having a photomultiplier tube (PMT) 96, as shown in FIG. 1B, or a photodiode 38, as shown in FIG. 1C.

As also shown in FIGS. 1B and 1C the apparatus 12 is part of a system for analyzing a sample. The system comprises a structure 50, also referred to herein as a housing, which is engaged (i.e., attached) to the read head 28, the detector 36, a power source 44, and a movable cartridge support 52. The movable cartridge support 52 positions the cartridge 10 within the apparatus 12 and is capable of supporting a plurality of cartridges and aligning each cartridge with the read head 28 and the detector 36. The cartridge 10 has a coupler 46 for providing a current supply from the power source 44 to the light source 18. Preferably, the cartridge 10 is mounted onto the support 52 and a plug terminating the electronics inside of the cartridge 10 is connected with a socket in the support 52. At the socket, several low voltage output lines of the power source 44 are available and interface lines with the main apparatus controller. The coupler 46 functions in connecting the cartridge 10 with other components in the apparatus 12, such as for receiving low DC voltage for the cartridge light source 18 and other electronics; establishing control lines for LED current adjustment; establishing control lines for cartridge recognition; data lines (e.g., an electronic bus) for detectors within the cartridge 10 (e.g., a photodiode for sending measured data to a controller); and synchronization lines for synchronizing pulses of the light source 18 with the data acquisition from detector(s) and other circuitry within the apparatus 12, such as photon counting circuitry in the main apparatus controller. Preferably, the coupler 46 is made from two parts, a printed circuit board that extends along the cartridge support 52, providing a socket for one or more cartridges 10, and a flexible flat cable at the end, bridging the gap to the main apparatus controller (flexible, because the cartridge support 52 can be moved). The electronic bus, or data line function is designed as of the type SPI (serial peripheral interface).

The system may also have a sample support carrier 54, such as a microplate scanning stage, attached to the structure for moving the sample support 17 either horizontally or vertically within the housing (e.g., structure 50).

Referring now to FIG. 1B, in certain embodiments, such as a cartridge 10 that is used for a fluorescence application, the emitting light 32 is collected from the target 14 by the read head 28 and collimated back into the cartridge 10. The cartridge 10 has a second optical system 34, which receives the emitted light 32 from the read head 28 and directs the emitted light 32 from the sample 16 to the detector 36. The emitting light 32 received from the read head 28 is transmitted through the reflector 26, and is then directed with a reflector 48 towards the cartridge exit 40, which interfaces with the detector 36 via a detector port 49. Before exiting the cartridge 10, the emitted light 32 is filtered through a filter 42, such as a bandpass filter, to reject contributions of excitation light being scattered back from the read head 28 and the sample 16. The entire path after the emitted light 32 has passed through the reflector 26 is optically shielded from those areas of the cartridge 10 which may be floated with diffuse scatter of exciting light 20.

Referring now to FIG. 1C, in certain embodiments, a cartridge 10, such as a cartridge that is used for an absorbance application, is positioned in the apparatus 12 in opposite to the detector 36. According to this embodiment, the exciting light 20 is transmitted through the sample 16 and sample support carrier 54 via an aperture 56 (i.e., a window or light transparent portion) in the sample support carrier 54 and an aperture 58 (i.e., a window or light transparent portion) in the sample support 17. Emitting light 32 from the target 14 is directed to the detector 36 (containing, e.g., a photodiode 38). The configuration of the cartridge 10 for measuring absorbance as shown in FIG. 1C is shown by way of example and other configurations are possible, for example, the cartridge 10 may be alternately positioned within the apparatus 12, such as in the same approximate plane as the detector 36 (e.g., side-by-side), and the emitting light 32 may be relayed to the detector 36, such as with a light guide, as will be understood by those of skill in the art with reference to this disclosure.

The one or more light sources 18 housed in the cartridge 10 may be selected from suitable light sources known to those of skill in the art such as light emitting diodes (LEDs), laser-diodes, and a Xenon flash lamp module. Preferably, when the cartridge 10 is used for a fluorescence application, such as shown in FIG. 1B, the light source 18 is one or more LED light sources. Preferred LED light sources are obtained from Lumileds, San Jose, Calif., US (for various peak wavelengths between 350 nm and 700 nm; Luxeon Star, Nichia, Tokushima, Japan, for various peak wavelengths between 350 nm and 700 nm; and Roithner-Laser, Vienna, Austria, for various peak wavelengths between 350 nm and 700 nm. Preferably, when the cartridge 10 is used for an absorbance application, such as shown in FIG. 1C, the light source 18 is a Xenon flash lamp module. Preferred Xenon flash lamp modules are obtained from Perkin Elmer Optoelectronics, Fremont, Calif., US, product name RSL3100; and Hamamatsu Photonics, Japan, product name L9455.

Figure 1E:
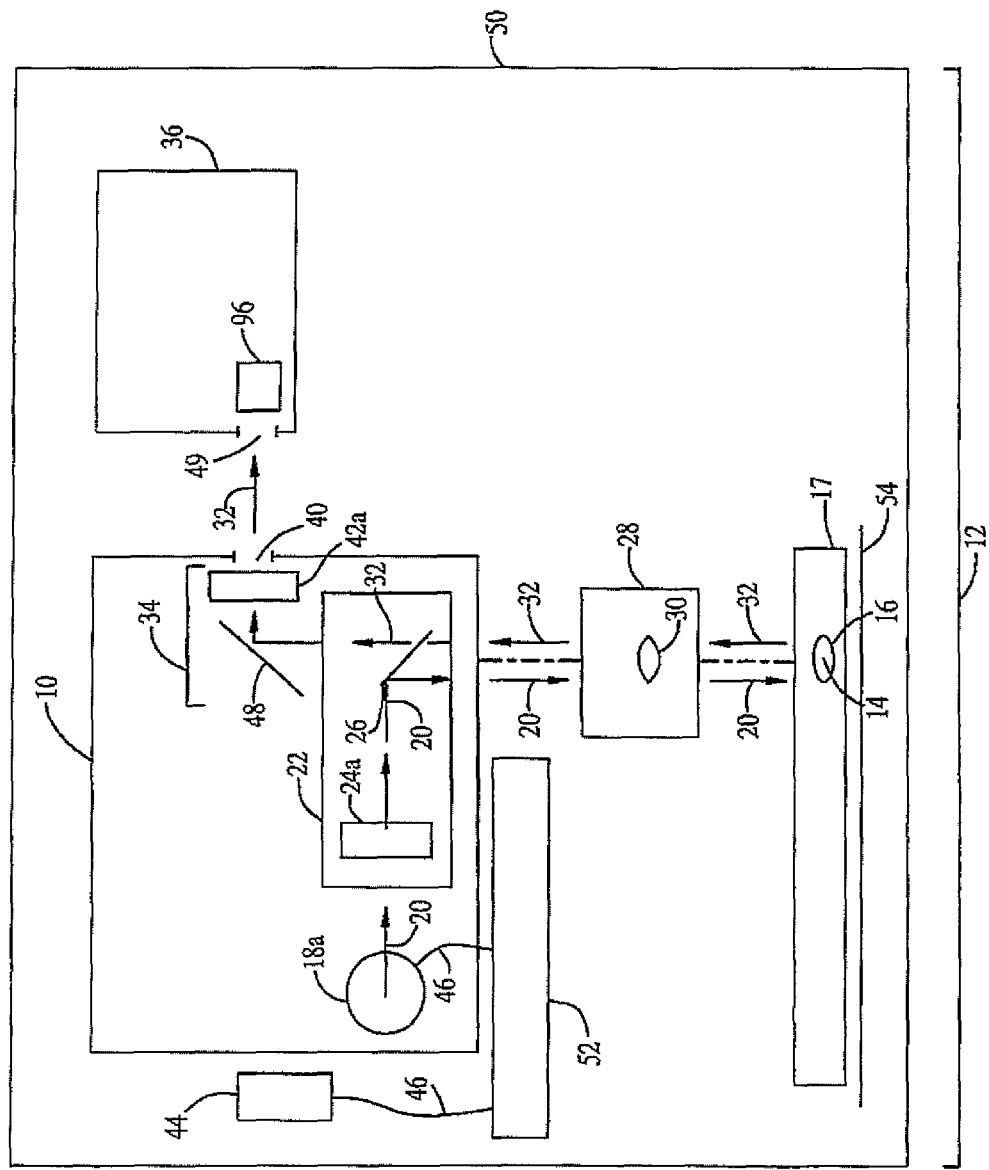
FIG. 1E is a schematic view of the wavelength-tunable cartridge of FIG. 1D loaded into an apparatus, according to another embodiment of the present disclosure.

FIG. 1D is a schematic view of an example of a wavelength-tunable cartridge 10 according to another embodiment. FIG. 1E is a schematic view of the wavelength-tunable cartridge 10 illustrated in FIG. 1D loaded into an apparatus 12. The wavelength-tunable cartridge 10 may be utilized in conjunction with the apparatus 12 as a system for analyzing a target 14 in a sample 16. In the present embodiment, the wavelength-tunable cartridge 10 is useful particularly for fluorescence applications. Like the cartridges described above and illustrated in FIGS. 1A, 1B and 1C, the wavelength-tunable cartridge 10 is designed to be removably engaged with the apparatus 12, and may be replaced or exchanged with other cartridges of the same or different type.

The wavelength-tunable cartridge 10 includes an adjustable light source assembly 18a. The light source assembly 18a includes a plurality of light sources 19 mounted at (supported by) a movable light source support 21, and a light source support drive device 23 (or light source support drive 23) communicating with the light source support 21. Each light source 19 is configured for producing an exciting light 20, when such light source 19 is selected for active operation in the manner described below. In some embodiments, each light source 19 has one or more emission characteristics that are different than the emission characteristic(s) of the other light sources 19. For instance, each light source 19 may be configured for producing the exciting light 20 in a different wavelength band (or at a different peak, or center, wavelength) than the other light sources 19. In some embodiments, however, the wavelength band of one or more of the light sources 19 may overlap to some degree with the wavelength band of one or more of the other light sources 19. The respective wavelength bands produced by the light sources 19 may be relatively narrow wavelength bands, relatively wide (broad) wavelength bands, or a combination of both narrow and broad wavelengths. For example, the array of light sources 19 may include light sources 19 producing light according to one or more of the following spectra: ultraviolet (UV) light of relatively long wavelengths, near UV light, purple light, blue light, green light, yellow light, white (broadband) light, orange or amber light, red light, near infrared (IR) light, and/or IR light of relatively short wavelengths. The light sources 19 collectively may cover a broad spectrum of available wavelengths, from shorter wavelengths to longer wavelengths, such that a desired wavelength band for the exciting light 20 is attained by selecting an appropriate one of the light sources 19 for active operation. Generally, no limitation is placed on the number of light sources 19 utilized. In one example fifteen light sources 19 are utilized, although the number may be less than or greater than fifteen. Generally, the light sources 19 may be any type of light sources configured for producing an exciting light 20, a few examples being light emitting diodes (LEDs) and laser diodes (LDs).

The light source support 21 may be configured for movement of any type. In one example, the light source support 21 may be rotatable about an axis 25 and thus may be or include, for example, a wheel or carousel. In another example, the light source support 21 may be linearly translatable in one dimension or two dimensions (e.g., X-Y) and thus may be or include, for example, a rail, slide, stage or platform. The light source support 21 is configured to move a selected one of the light sources 19a into a light source operating position 27. When located at the light source operating position 27, the selected light source 19a is in optical alignment (or optical communication) with other components of the wavelength-tunable cartridge 10 and may be actively operated to produce the exciting light 20. Thus, at the light source operating position 27, the exciting light 20 emitted by the selected light source 19a is able to be filtered and directed to the sample 16.

The light source support drive 23 may be any device or system configured for moving (e.g., rotating or translating) the light source support 21. As non-limiting examples, the light source support drive 23 may be or include a stepper motor (or micro-stepper motor) or a solenoid. The axis 25 may also schematically represent a linkage (or connection, or coupling) between the light source support drive 23 and the light source support 21. The linkage generally may be any type of linkage that enables powered, controlled actuation of the light source support 21. Hence, the linkage may be a mechanical or physical linkage, or may be a non-contacting linkage such as a magnetic or electromagnetic coupling.

As also shown in FIGS. 1D and 1E, the wavelength-tunable cartridge 10 also includes a first optical system 22. The first optical system 22 includes components for directing the exciting light 20 from the selected light source 19a to the sample 16. In the illustrated embodiment, the first optical system 22 includes an adjustable excitation filter assembly 24a and one or more light-guiding components (or optics) as needed, such as reflectors 11 and 26. In the present example, the reflector 26 may be a dichroic beamsplitter configured for reflecting the exciting light 20 and transmitting the emitted light 32 (or emitting light 32). The excitation filter assembly 24a includes a plurality of excitation filters 29 mounted at (supported by) a movable excitation filter support 31, and an excitation filter support drive device 33 (or excitation filter support drive 33) communicating with the excitation filter support 31.

Each excitation filter 29 is configured for passing (transmitting) a particular wavelength or wavelength band (and blocking other wavelengths) of the exciting light 20, when such excitation filter 29 is selected for positioning in the path of the exciting light 20 in the manner described below. In some embodiments, the excitation filter 29 when selected passes only the wavelength band necessary to excite the sample 16 of interest. In some embodiments, each excitation filter 29 has one or more optical filtering characteristics (wavelength-transmitting and/or wavelength blocking characteristics) that are different than the optical filtering characteristic(s) of the other excitation filters 29. For instance, each excitation filter 29 may be configured for passing a wavelength or wavelength band that is different from the respective wavelengths or wavelength bands passed by the other excitation filters 29. In some embodiments, however, the wavelength band passed by one or more of the excitation filters 29 may overlap to some degree with the wavelength band passed by one or more of the other excitation filters 29. The respective wavelength bands passed by the excitation filters 29 may be relatively narrow wavelength bands, relatively wide (broad) wavelength bands, or a combination of both narrow and broad wavelength bands. Generally, no limitation is placed on the number of excitation filters 29 utilized. In one example seven excitation filters 29 are utilized, although the number may be less than or greater than seven. A given excitation filter 29 may be compatible for use with one or more of the light sources 19.

The excitation filters 29 typically are bandpass filters, although depending on the wavelengths to be passed may alternatively be low-pass or high-pass filters. In the present embodiment, the excitation filters 29 are adjustable (tunable) filters, and more specifically are tiltable (rotatable) filters. Generally, the excitation filters 29 may be any type of optical filters (e.g., interference filters, dichroic filters) configured such that the wavelength band passed by the excitation filter 29 is tunable by tilting the excitation filter 29 a selected number of degrees from the normal-incidence position (i.e, the position at which the beam of exciting light 20 is normal to the face of the excitation filter 29). Preferably, the excitation filter 29 is configured such that its spectral performance remains relatively constant over its entire tuning (tilting) range. In some embodiments, the excitation filter 29 is tunable up to 60° from the normal-incidence position. In one example, the excitation filters 29 may be, or be similar to, filters of the VersaChrome™ tunable bandpass filter family commercially available from Semrock, Inc., Rochester, N.Y.

The excitation filter support 31 may be configured for movement of any type. In one example, the excitation filter support 31 may be rotatable about an axis 35 and thus may be or include, for example, a wheel or carousel. In another example, the excitation filter support 31 may be linearly translatable in one dimension or two dimensions (e.g., X-Y) and thus may be or include, for example, a rail, slide, stage or platform. The excitation filter support 31 is configured to move a selected one of the excitation filters 29a into an excitation filter operating position 37. When located at the excitation filter operating position 37, the selected excitation filter 29a is in optical alignment (or optical communication) with the selected light source 19a located at the light source operating position 27 (via any light-guiding components as needed for a particular design layout, such as the reflector 11), and thus is able to filter the exciting light 20.

The excitation filter support drive 33 may be any device or system configured for moving (e.g., rotating or translating) the excitation filter support 31. As non-limiting examples, the excitation filter support drive 33 may be or include a stepper motor (or micro-stepper motor) or a solenoid. The axis 35 may also schematically represent a linkage (or connection, or coupling) between the excitation filter support drive 33 and the excitation filter support 31. The linkage generally may be any type of linkage that enables powered, controlled actuation of the excitation filter support 31. Hence, the linkage may be a mechanical or physical linkage, or may be a non-contacting linkage such as a magnetic or electromagnetic coupling.

The excitation filter assembly 24a also includes an excitation filter tilt drive device 39 (or excitation filter tilt drive 39). The tilt drive 39 is configured for interacting with the selected excitation filter 29a when the selected excitation filter 29a is located at the excitation filter operating position 37. Specifically, the tilt drive 39 is configured for tilting (adjusting the angular position of) the selected excitation filter 29a about a tilt axis 41 to a desired tilt angle relative to the beam of the exciting light 20. In FIG. 1D, the reflector 11 is representative of light-guiding optics between the selected light source 19a and the selected excitation filter 29a. The exciting light 20 is directed by the reflector 11 (and/or other light-guiding optics) such that the exciting light 20 propagates in the horizontal direction (from the perspective of FIG. 1D) at the point it is incident on, and passes through, the selected excitation filter 29a. In FIG. 1D, the selected excitation filter 29a is shown as being positioned at a tilt angle (angle of incidence) corresponding to the selected excitation filter 29a being orthogonal (or normal, or 90°) to the beam of exciting light 20. This angular position of the selected excitation filter 29 may be considered to be a non-tilted position, or normal-incidence position. The normal-incidence position illustrated in FIG. 1D may in turn be considered to be a tilt angle of 0° (zero degrees) relative to the tilt axis 41—that is, the degree of tilting about the tilt axis 41 is zero. As noted above, in some implementations the selected excitation filter 29a is tiltable by as much as 60° from the zero-degree normal-incidence position. As the tilt angle is increased from 0°, the center wavelength ($\lambda_c$) of the selected excitation filter 29a decreases. In some implementations, the effect of tilt angle (θ) on the center wavelength ($\lambda_c$) may be approximated by the following relation:

$$\lambda_c(\theta)=\lambda_0\sqrt{1-(\sin\theta/n^*)^2},$$

where $\lambda_0$ is the center wavelength at normal incidence and n* is the effective index of refraction of the selected excitation filter 29a, which varies with tilt angle and polarization.

In one embodiment, the excitation filters 29 are retained in or on respective filter holders that may be contacted by the tilt drive 39 without a risk of damaging the excitation filters 29. The tilt drive 39 may include an actuator (e.g., a wire, rod, aim, or other structure) that rotates about an axis that is in-line with the tilt axis 41. The actuator may be rotated into contact with one end of the filter holder associated with the selected excitation filter 29a when the selected excitation filter 29a is located at the excitation filter operating position 37. One or more springs may bias the selected excitation filter 29a to rotate toward the normal-incidence position. The spring(s) may be in contact with the filter holder at an end opposite to the end at which the actuator contacts the filter holder, with the tilt axis 41 being located between these opposing ends. At the excitation filter operating position 37, to increase the tilt angle to a value greater than 0° (normal incidence), the actuator may be rotated in a first direction into contact with the filter holder and thereby rotate the selected excitation filter 29a against the biasing force of the spring(s). The selected excitation filter 29a may then be held at the desired tilt angle between the counteracting forces of the actuator and the spring(s). To reduce the tilt angle, the actuator may be rotated in a second direction opposite to the first direction, thus allowing the spring(s) to pull on the opposite end of the filter holder, and thereby rotating the selected excitation filter 29a about the tilt axis 41 back toward the normal-incidence position.

As also shown in FIGS. 1D and 1E, the wavelength-tunable cartridge 10 may also include a second optical system 34. The second optical system 34 includes components for receiving the emitted light 32 from the sample 16 and directing the emitted light 32 to an optical cartridge-output detector 36 (or optical output detector 36). For this purpose, the second optical system 34 may include one or more light-guiding components (or optics) as needed, such as a reflector 13 (FIG. 1D) and/or reflector 48 (FIG. 1E), and one or more filters. In some embodiments, the second optical system 34 may include a single filter such as the filter 42 described above and illustrated in FIG. 1B. In the embodiment illustrated in FIGS. 1D and 1E, the second optical system 34 includes an adjustable emission filter assembly 42a. The emission filter assembly 42a includes a plurality of emission filters 43 mounted at (supported by) a movable emission filter support 45, and an emission filter support drive device 47 (or emission filter support drive 47) communicating with the emission filter support 45.

Each emission filter 43 is configured for passing (transmitting) a particular wavelength or wavelength band (and blocking other wavelengths) of the emitted light 32, when such emission filter 43 is selected for positioning in the path of the emitted light 32 in the manner described below. In some embodiments, the emission filter 43 when selected passes only the wavelength band necessary to separate background light from the specific wavelengths generated by the sample 16 being interrogated. In some embodiments, each emission filter 43 has one or more optical filtering characteristics that are different than the optical filtering characteristic(s) of the other emission filters 43. For instance, each emission filter 43 may be configured for passing a wavelength or wavelength band that is different from the respective wavelengths or wavelength bands passed by the other emission filters 43. In some embodiments, however, the wavelength band passed by one or more of the emission filters 43 may overlap to some degree with the wavelength band passed by one or more of the other emission filters 43. The respective wavelength bands passed by the emission filters 43 may be relatively narrow wavelength bands, relatively wide (broad) wavelength bands, or a combination of both narrow and broad wavelength bands. Generally, no limitation is placed on the number of emission filters 43 utilized. In one example seven emission filters 43 are utilized, although the number may be less than or greater than seven. The emission filters 43 typically are bandpass filters, although depending on the wavelengths to be passed may alternatively be low-pass or high-pass filters. In the present embodiment, the emission filters 43 are adjustable (tunable) filters, and more specifically are tiltable (rotatable) filters. Generally, the emission filters 43 may be any type of optical filters that are tunable by tilting the emission filter 43 a selected number of degrees from the normal-incidence position, and thus may have the same or similar configuration and material composition as the excitation filters 29 described above.

The emission filter support 45 may be configured for movement of any type. In one example, the emission filter support 45 may be rotatable about an axis 49 and thus may be or include, for example, a wheel or carousel. In another example, the emission filter support 45 may be linearly translatable in one dimension or two dimensions (e.g., X-Y) and thus may be or include, for example, a rail, slide, stage or platform. The emission filter support 45 is configured to move a selected one of the emission filters 43a into an emission filter operating position 51. When located at the emission filter operating position 51, the selected emission filter 43a is in optical alignment (or optical communication) with the beam of emitted light 32 and thus is able to filter the exciting light 20. At the emission filter operating position 51, the selected emission filter 43a is also in optical alignment with the output detector 36, via any light-guiding components as needed, such as the reflector 13 and/or 48.

The emission filter support drive 47 may be any device or system configured for moving (e.g., rotating or translating) the emission filter support 45. As non-limiting examples, the emission filter support drive 47 may be or include a stepper motor (or micro-stepper motor) or a solenoid. The axis 49 may also schematically represent a linkage (or connection, or coupling) between the emission filter support drive 47 and the emission filter support 45. The linkage generally may be any type of linkage that enables powered, controlled actuation of the emission filter support 45. Hence, the linkage may be a mechanical or physical linkage, or may be a non-contacting linkage such as a magnetic or electromagnetic coupling.

The emission filter assembly 42a also includes an emission filter tilt drive device 53 (or emission filter tilt drive 53). The tilt drive 53 is configured for interacting with the selected emission filter 43a when the selected emission filter 43a is located at the emission filter operating position 51. Specifically, the tilt drive 53 is configured for tilting (adjusting the angular position of) the selected emission filter 43a about a tilt axis 55 to a desired tilt angle relative to the beam of the emitted light 32. In FIG. 1D, the selected emission filter 43a is shown as being positioned at a tilt angle corresponding to the selected emission filter 43a being normal to the beam of emitted light 32. This angular position of the selected emission filter 43a may be considered to be a non-tilted position, or normal-incidence position. The normal-incidence position illustrated in FIG. 1D may in turn be considered to be a tilt angle of 0° relative to the tilt axis 55. In some implementations the selected emission filter 43a is tiltable by as much as 60° from the zero-degree normal-incidence position.

In some embodiments, the emission filter assembly 42a (including the emission filter tilt drive device 53) is structured and operates in the same way as the excitation filter assembly 24a (including the excitation filter tilt drive device 39).

In one non-limiting example, the set of light sources 19 collectively covers a spectral range of 360 nm to 790 nm. In the same example or in another non-limiting example, the set of excitation filters 29 collectively covers a spectral range of 360 nm to 790 nm, with a wavelength increment of 1 nm. In the same example or in another non-limiting example, the set of emission filters 43 collectively covers a spectral range of 400 nm to 850 nm, with a wavelength increment of 1 nm.

TABLE 1 below provides another non-limiting example of the wavelength-tunable cartridge 10 provided with a set of fifteen LEDs as the light sources 19, seven tunable excitation filters 29, and seven tunable emission filters 43. TABLE 1 provides the center wavelength ($\lambda_c$) and bandwidth (BW) emitted by each light source 19, the center wavelength and bandwidth transmitted by each excitation filter 29 ("Ex filter"), and the center wavelength and bandwidth transmitted by each emission filter 43 ("Em filter"). Each center wavelength given in TABLE 1 may be considered to be at, or approximately at, the center of the associated bandwidth.

TABLE 1

|  | $\lambda_c$ (nm) | BW (nm) |
|---|---|---|
| LED #1 | 365 | 15 |
| LED #2 | 375 | 15 |
| LED #3 | 385 | 15 |
| LED #4 | 400 | 26 |
| LED #5 | 435 | 31 |
| LED #6 | 470 | 25 |
| LED #7 | 505 | 25 |
| LED #8 | 525 | 45 |
| LED #9 | 590 | 100 |
| LED #10 | 625 | 18 |
| LED #11 | 660 | 18 |
| LED #12 | 680 | 25 |
| LED #13 | 720 | 30 |
| LED #14 | 750 | 30 |
| LED #15 | 780 | 30 |
| Ex filter #1 | 400 | 16 |
| Ex filter #2 | 448 | 15 |
| Ex filter #3 | 501 | 15 |
| Ex filter #4 | 561 | 14 |
| Ex filter #5 | 627 | 14 |
| Ex filter #6 | 703 | 13 |
| Ex filter #7 | 790 | 12 |
| Em filter #1 | 448 | 15 |
| Em filter #2 | 501 | 15 |
| Em filter #3 | 561 | 14 |
| Em filter #4 | 627 | 14 |
| Em filter #5 | 703 | 13 |
| Em filter #6 | 790 | 12 |
| Em filter #7 | 850 | 11 |

In another embodiment of the wavelength-tunable cartridge 10, first optical system 22 may include a single light source and a single filter, such as the light source 18 and filter 24 described above and illustrated in FIG. 1B, while the second optical system 34 includes an adjustable emission filter assembly such as the emission filter assembly 42a described above and illustrated in FIG. 1D. In yet another embodiment of the wavelength-tunable cartridge 10, the first optical system 22 may include an adjustable light source assembly such as the light source assembly 18a described above and illustrated in FIG. 1D, and a single filter such as the filter 24 illustrated in FIG. 1B, while the second optical system 34 includes an adjustable emission filter assembly such as the emission filter assembly 42a illustrated in FIG. 1D.

Referring to FIG. 1E, the apparatus 12 may include a structure or housing 50 that encloses the various components of the apparatus 12, including the wavelength-tunable cartridge 10 and any other cartridges installed in the apparatus 12. The apparatus 12 may also include a read head 28. The read head 28 may be configured as described above in conjunction with FIGS. 1A, 1B and 1C, and thus may include a lens 30 and/or other optics. The lens 30 may be movable or otherwise adjustable to focus exciting light 20 and emitted light 32 properly. One or more samples 16 may be held or positioned at (on, in) a sample support 17. The apparatus 12 may include a sample support carrier 54 at which the sample support 17 is mounted. The sample support carrier 54 may be movable into and out from the apparatus 12, such as through an access panel or door (not shown), to facilitate loading and removing the sample support 17. The sample support carrier 54 may also be movable in one or more directions as necessary for (sequentially) moving each sample 16 held by the sample support 17 into optical alignment with the read head 28.

The apparatus 12 may also include a movable cartridge support 52 on which the wavelength-tunable cartridge 10 is loaded. The cartridge support 52 may be movable into and out from the apparatus 12, such as through an access panel or door (not shown), to facilitate loading and removing the wavelength-tunable cartridge 10. The cartridge support 52 may also be movable in one or more directions as necessary for moving the wavelength-tunable cartridge 10 into optical alignment (or optical communication) with the output detector 36. The cartridge support 52 may also be movable in one or more directions as necessary for moving the wavelength-tunable cartridge 10 into optical alignment (or optical communication) with the read head 28. Alternatively or in addition to the cartridge support 52 being movable to align the wavelength-tunable cartridge 10 with the read head 28, the read head 28 may be configured so as to be movable into alignment with the exciting light 20 exiting the wavelength-tunable cartridge 10 and the emitted light 32 entering the wavelength-tunable cartridge 10.

The cartridge support 52 may be configured for receiving, simultaneously or sequentially, one or more cartridges in addition to the wavelength-tunable cartridge 10, and holding all cartridges simultaneously (i.e., concurrently) in the apparatus 12. For this purpose, the cartridge support 52 may be structured so as to define a plurality of cartridge positions into which cartridges may be separately installed. Depending on the types of cartridges being utilized, a given cartridge may occupy a single cartridge position or two or more adjacent cartridge positions. When a plurality or stack of cartridges is loaded on the cartridge support 52, two or more of these cartridges may be of the type requiring optical communication with the output detector 36, the read head 28, or both the output detector 36 and read head 28. Accordingly, when this type of cartridge is to be put into use in the apparatus for a given measurement, the cartridge support 52 may be configured for aligning that particular cartridge with the output detector 36 and/or read head 28 as necessary. One example of a cartridge support configured for handling a plurality of cartridges concurrently is described below in conjunction with FIG. 10.

Figure 10:
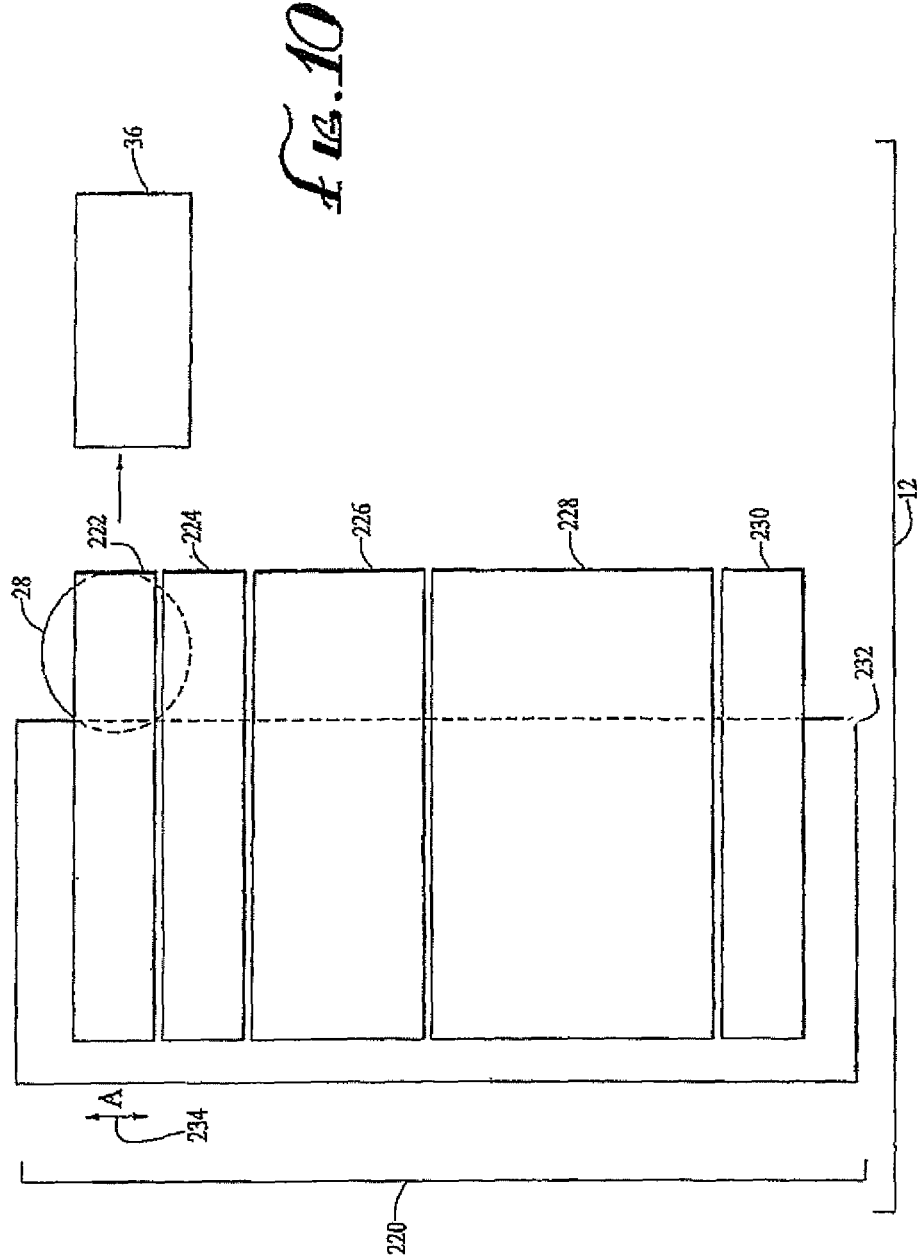
FIG. 10 is a schematic top view of a cartridge system according to an embodiment of the present invention.

In some embodiments, the apparatus 12 has a top-and-bottom configuration in which one or more cartridges are located above the sample support 17 (e.g., top-reading detection position) and one or more cartridges are located below the sample support 17 (e.g., bottom-reading detection position). One example of a top-and-bottom configuration is described below in conjunction with FIG. 11. A cartridge support configured for handling a plurality of cartridges concurrently, for example as illustrated in FIG. 10, may be located above the sample support 17 or below the sample support 17. Moreover two cartridge supports, each configured for handling a plurality of cartridges concurrently, may be respectively located above the sample support 17 and below the sample support 17. The wavelength-tunable cartridge 10 may be installed in either the top-reading detection position or the bottom-reading detection position, with or without other cartridges also installed in these positions.

The apparatus 12 may also include a power source 44, couplers 46, and components associated with power and data interfaces between the wavelength-tunable cartridge 10 and the apparatus 12 (e.g., one or more plugs; sockets; circuit boards or substrates; lines, busses and/or flexible cables for data, control signals and/or power; memory containing information regarding cartridge recognition, application-specific parameters, etc.), as described above in conjunction with FIGS. 1A, 1B and 1C and described below in conjunction with FIG. 10. The power source 44 may be configured to provide electrical power to several components of the wavelength-tunable cartridge 10, such as the light source support drive 23, selected light source 19a, excitation filter support drive 33, excitation filter tilt drive 39, emission filter support drive 47, and/or emission filter tilt drive 53. The apparatus 12 may include a main controller, with hardware, firmware and/or software components, configured for monitoring, controlling and synchronizing (or coordinating) the respective operations of such components. The light source support drive 23, excitation filter support drive 33, excitation filter tilt drive 39, emission filter support drive 47, and emission filter tilt drive 53 may be adjustable (movable) independently of each other. Hence, the axes 25, 33, 41, 49 and 55 may be independent (or separate) axes.

A non-limiting example of implementing a method for analyzing a target in a sample utilizing the wavelength-tunable cartridge 10 will now be described, primarily with reference to FIGS. 1D and 1E. In this example, the method relates to fluorescence measurement. The sample support 17 containing one or more samples 16 is loaded onto the support carrier 54. The support carrier 54 is operated to move the sample support 17 into the interior of the housing 50 of the apparatus 12, and to optically align the sample 16 (or a selected one of several samples 16) with the read head 28. Alternatively or additionally, the read head 28 is operated to move into optical alignment with the sample 16. The wavelength-tunable cartridge 10 is loaded onto the cartridge support 52, with or without other cartridges. The cartridge support 52 is operated to move the wavelength-tunable cartridge 10 into the interior of the housing 50, and to optically align the wavelength-tunable cartridge 10 with the read head 28 and/or the output detector 36 as necessary.

Depending on various factors such as the composition of the sample 16, the type of fluorophore (if any) or other label associated with the sample 16, and the type of measurement desired, a wavelength band for the exciting light 20 to be utilized for irradiating the sample 16 (or target 14), and a wavelength band for the emitted light 32 to be read by the output detector 36, are selected (or determined, or calculated). Based on the selection, determination or calculation of these wavelength bands, the excitation optics and the emission optics of the wavelength-tunable cartridge 10 are configured (tuned) as needed, by adjusting the light source assembly 18a, excitation filter assembly 24a and emission filter assembly 42a. Specifically, an appropriate combination comprising one of the light sources 19, one of the excitation filters 29, and one of the emission filters 43 is selected. The combination is selected by operating the light source assembly 18a to move the selected light source 19a into the light source operating position 27, operating the excitation filter assembly 24a to move the selected excitation filter 29a into the excitation filter operating position 37, and operating the emission filter assembly 42a to move the selected emission filter 43a into the emission filter operating position 51. In a typical embodiment, the selected excitation filter 29a is in its normal-incidence position at the time it is moved into the excitation filter operating position 37, and the selected emission filter 43a likewise is in its normal-incidence position at the time it is moved into the excitation filter operating position 37. Thus, configuring the wavelength-tunable cartridge 10 may also entail operating the excitation filter assembly 24a to move the selected excitation filter 29a to a desired non-zero tilt angle, and operating the emission filter assembly 42a to move the selected emission filter 43a to a desired non-zero tilt angle.

After the wavelength-tunable cartridge 10 has been configured as desired, the selected light source 19a is activated to produce the exciting light 20 at the desired (unfiltered) wavelength band. The exciting light 20 is directed to the selected excitation filter 29a, utilizing optics (e.g., reflector 11) as needed, whereby the exciting light 20 passes through the selected excitation filter 29a and is filtered thereby in accordance with the selected tilt angle. The filtered exciting light 20 is then reflected by the reflector 26 and directed out from the wavelength-tunable cartridge 10 to the read head 28, at the determined wavelength band. The read head 28 directs the filtered exciting light 20 to the sample 16, which in response emits the emitted light 32. The read head 28 collects the emitted light 32 and directs it into the wavelength-tunable cartridge 10. The emitted light 32 is directed, by optics if needed, to the selected emission filter 43a, whereby the emitted light 32 passes through the selected emission filter 43a and is filtered thereby in accordance with the selected tilt angle. The filtered emitted light 32 is then reflected by the reflector 13 (FIG. 1D) and directed out from an aperture 40 of the wavelength-tunable cartridge 10 to the output detector 36, at the determined wavelength band. At the output detector 36, the filtered emitted light 32 is read by a detector unit 96 (photodiode, photomultiplier tube, etc.), after which the optical signal may be converted to an electrical signal, which in turn may be further conditioned and processed as needed to produce useful measurement data pertaining to the sample 16 being interrogated.

It will be understood that the method described above may be modified as necessary to account for differently configured wavelength-tunable cartridges 10, such as when the light source assembly 18a, excitation filter assembly 24a and/or emission filter assembly 42a are not provided or not utilized in a particular analysis.

One or more embodiments of the wavelength-tunable cartridge 10 described above may combine the advantages of interference filters with monochromators. The diameter of the light beams may be the same as or larger than those utilized in conventional filter-based multimode readers, thus increasing sensitivity. At the same time, the optical filtering characteristics of the excitation filters 29 and emission filters 43 may be the same as or better than those utilized in conventional filter-based multimode readers. The enhanced tunability of the wavelength-tunable cartridge 10 may enable fluorescence-based analyses to be performed with higher sensitivity, scanning speeds, signal-to-background (S/B) ratio, and detection limits, and greater linear dynamic range (LDR), as compared to known fluorescence-based readers. Moreover, the broad spectral range covered by the wavelength-tunable cartridge 10 enables the same wavelength-tunable cartridge 10 to be utilized in conjunction with virtually any fluorophore compatible with the wavelength range(s) provided by the wavelength-tunable cartridge 10, and eliminates or significantly reduces the need to employ different cartridges for different analyses or different fluorescent labels. As noted above, the wavelength-tunable cartridge 10 is particularly useful for fluorescence-based measurements including, but not limited to, fluorescence intensity, fluorescence resonance energy transfer (FRET), time-resolved fluorescence, and fluorescence polarization.

Referring now to FIG. 2, another embodiment of the apparatus 12 for analyzing a target 14 in a sample 16 is shown. According to this embodiment, the apparatus 12 has a source intensity monitoring cartridge 60 with a light source 18 and a first optical system 22 which has components for directing an exciting light beam 20 to a sample 16 via a read head, as described with respect to FIG. 1B. The cartridge 60 is designed to be removably engaged with apparatus 12 via the movable cartridge support 52. In certain embodiments, the cartridge 60 has a second optical system 34 (not shown), as described with respect to FIG. 1B, which receives emitting light 32 from the sample 16 via the read head (not shown) and directs the emitting light 32 from the sample 16 to the detector 36.

According to the embodiment shown in FIG. 2, during or prior to signal detection at the detector 36, the exciting light beam 20 is passed through an excitation filter 24 and a portion of the exciting light beam 20 is reflected onto a light source detector 62 (e.g., a photodiode) with a partially reflecting mirror 64 as reflected light 66. Electronic circuitry 68 measures the intensity level of the reflected light 66. The measured intensity level of the reflected light 66 is used to stabilize the output of the light source 18 via a feedback loop 70.

In another embodiment shown in FIG. 2, when analyzing a target 14 in a sample 16 with the detector 36 using a fluorescence method, as described with respect to FIG. 1B, the electronic path 72a, 72b, and 72c may be applied to extend the generic dynamic range of the detector 36. According to this embodiment, the light source 18 is first adjusted to a maximum intensity, and the intensity of the emitting light 32 is tested (for quite a short pre read time to give a pre read value) at the detector 36. The main controller 74 receives the tested emitting light signal from the detector 36 via path 72c and may adjust the intensity of the exciting light 20 (i.e., the source intensity) by addressing the controller 68 via control line 72a and 72b. Preferably, when detecting a superthreshold signal at detector 36, the main controller 74 reduces the intensity of the exciting light 20 by adjusting the power to light source 18 according to the pre read value. In this preferred embodiment, the target 14 is measured with a longer read time, as selected by the user, and the intensity of the signal from the emitting light 32 found at the detector 36 is normalized with the actual value of the intensity of the exciting light 20, because the intensity of the emitting light 32 changes according to the intensity of the exciting light 20. Thus, the read out becomes comparable with measurement values taken at other light source intensity levels.

In fluorescence applications, the LED light source(s) are typically supplied with constant current for reading of prompt fluorescence, where prompt fluorescence is differentiated from time delayed fluorescence reading, e.g., in prompt fluorescence, the fluorescence emission is instantaneously gone when the light source is switched off—unless operating on nanosecond time scales (fluorescence labels having typical decay times of about 1 to about 10 nanoseconds). In other fluorescence applications using a light source 18 that can be pulsed (e.g., LEDs, laser diodes, and Xenon flash lamps), enables the measurement of fluorescence with a time delay (i.e., "time-resolved," in connection with lanthanide ion labels having decay times between about 20 and about 2,000 microseconds). In such applications, the photon counting electronics, (to be thought as included in the detector 36) monitoring the sample emission are enabled (gated by the controller 74 via control line 72c) with a short time delay after the light source 18 has been switched off by controller 74 via control line 72a and 72b.

According to another embodiment, the wavelength-tunable cartridge 10 described above and illustrated in FIGS. 1D and 1E is configured to include the light source detector 62 and associated components (e.g., electronic circuitry 68, feedback loop 70, electronic path 72a, partially reflecting mirror or beamsplitter 64) described above and illustrated in FIG. 2. By this configuration, the intensity level of the exciting light 20 produced by the selected light source 19a (FIG. 1D) may be monitored and adjusted.

Referring now to FIG. 3, another embodiment of the apparatus 12 for analyzing a target 14 in a sample 16 is shown. According to the embodiment shown in FIG. 3, the apparatus 12 has a dual emission cartridge 80 that is capable of measuring dual label assays. The dual emission cartridge 80 is designed to be removably engaged with apparatus 12 via the movable cartridge support 52. Certain assays profit from measuring two different emission wavelengths at the same time (e.g., Fluorescence Resonance Energy Transfer (FRET) type assays), and measuring two different emission wavelengths at substantially the same time can result in a total time saving for the user due to the reduced read time.

According to the embodiment shown in FIG. 3, the apparatus 12 has a light source 18 which produces an exciting light 20, such as described with respect to FIG. 1B. The apparatus 12 additionally has a power source 44 and the cartridge 80 has a coupler 46 for providing a current supply to the light source 18 from the power source 44. The dual emission cartridge 80 has a first optical system 22 which has components, including an excitation filter 24, for directing the exciting light 20 to a sample 16 via a read head 28. The read head 28 directs the exciting light 20 toward the sample 16. The sample 16, containing the target 14, produces an emitting light 82. The dual emission cartridge 80 has a second optical system 84, which receives the emitting light 82 from the read head 28 and directs the emitting light 82 from the sample 16 to a detector 36. The emitting light 82 contains two wavelength bands 82a and 82b which are both passed through the reflector 26. The first wavelength band 82a is reflected by a beamsplitter 88 toward the detector 36 via a first emission filter 90 (e.g., a bandpass filter). The second wavelength band 82b is passed by the beamsplitter 88, and reflected at a mirror 92 toward the detector 36 via a second emission filter 94 (e.g., a bandpass filter). The detector 36 is a dual channel detector which preferably has two detectors 96 and 98, preferably photomultiplier tubes which are stacked to form the dual channel detector. In addition, the cartridge 80 has a dual exit port 100 and 102, which is aligned with the detectors 96 and 98 via detector ports 104 and 106. The detector ports 104 and 106 may include collecting lenses that focus the quasi collimated emission light onto the active area(s) of the detector 36, which is typically smaller than the emission light 82 beam diameter.

FIG. 3A is a schematic view of an example of a dual emission cartridge 80 provided with wavelength-tuning features, according to another embodiment of the present disclosure. The dual emission cartridge includes a first adjustable emission filter 90a and a second adjustable emission filter 94a. The first adjustable emission filter 90a and second adjustable emission filter 94a may have configurations similar to the emission filters 43 described above and illustrated in FIG. 1D. Hence, the first adjustable emission filter 90a and second adjustable emission filter 94a are movable about respective tilt axes, and may be actuated by one or more tilt drive devices. The dual emission cartridge 80, dual channel output detector 36, and other components illustrated in FIG. 3A may otherwise be configured similar to those described above and illustrated in FIG. 3.

Referring now to FIG. 4, another embodiment of the apparatus 12 for analyzing a target 14 in a sample 16 is shown. According to the embodiment shown in FIG. 4, the apparatus 12 has a dual emission dual excitation cartridge 110 that is equipped with a second light source 116. The cartridge 110 is designed to be removably engaged with apparatus 12 via the movable cartridge support 52. When light sources which can be pulsed are used, such as LEDs or laser diodes, the first and second light sources 18 and 116 may be electronically switched, and different wavelengths of light may be used to measure a sample. According to this embodiment, there is no need to mechanically switch between different wavelengths of light, which results in a saving of total measurement time.

According to the embodiment shown in FIG. 4, the apparatus 12 has a first light source 18 which produces a first exciting light 20 and a second light source 116 which produces a second exciting light 118. The apparatus 12 additionally has a power source 44 and the cartridge 110 has a coupler 46 for providing a current supply to light sources 18 and 116 from the power source 44. The dual emission dual excitation cartridge 110 has a first optical system 120 which has components, including a first excitation filter 122 and a second excitation filter 124, for directing the first and second exciting lights 20 and 118, respectively, to a beam combiner 126. The beam combiner 126 aligns the first and second exciting lights 20 and 118 to form a combined exciting light beam 128. The combined exciting light beam 128 is directed to the sample 16 via reflector 26 and read head 28. The sample 16, containing the target 14, produces an emitting light 82. The dual emission dual excitation cartridge 110 has a second optical system 84, as previously described with respect to FIG. 3, which receives the emitting light 82 from the read head 28 and directs the emitting light 82 from the sample 16 to detector 36.

In certain embodiments of the invention shown in FIG. 4, the dual emission dual excitation cartridge 110 is used to measure fluorescence polarization. According to this embodiment, the wavelengths of the first and second exciting lights 20 and 118 are essentially the same, and beam combiner 126 and beamsplitter 88 are polarizing cubes. The function of the second light source 116 is to determine the apparatus specific normalization factor for Fluorescence Polarization (G-Factor) by performing a calibration measurement.

FIG. 4A is a schematic view of an example of a dual emission, dual excitation cartridge 110 provided with wavelength-tuning features, according to another embodiment of the present disclosure. The dual emission, dual excitation cartridge includes a first light source 18a, a second light source 116a, a first adjustable excitation filter 122a, a second adjustable excitation filter 124a, a first adjustable emission filter 90a, and a second adjustable emission filter 94a. The first light source 18a and second light source 116a may be single light sources, or alternatively may be adjustable light source assemblies similar to the light source assembly 18a described above and illustrated in FIG. 1D. The first adjustable excitation filter 122a, second adjustable excitation filter 124a, first adjustable emission filter 90a, and second adjustable emission filter 94a may have configurations similar to the excitation filters 29 and emission filters 43 described above and illustrated in FIG. 1D. Hence, the first adjustable excitation filter 122a, second adjustable excitation filter 124a, first adjustable emission filter 90a, and second adjustable emission filter 94a are movable about respective tilt axes, and may be actuated by one or more tilt drive devices. The dual emission cartridge 110, dual channel output detector 36, and other components illustrated in FIG. 4A may otherwise be configured similar to those described above and illustrated in FIG. 4.

Referring now to FIG. 5, another embodiment of the apparatus 12 for analyzing a target 14 in a sample 16 is shown. According to the embodiment shown in FIG. 5, the apparatus 12 has a dual excitation cartridge 130 that is equipped with a second light source 116. The cartridge 130 is designed to be removably engaged with apparatus 12. As described with respect to FIG. 4, when light sources that can be pulsed are used, the first and second light sources 18 and 116 may be electronically switched, and different wavelengths of light can be used to measure a sample. According to the embodiment of the cartridge 130 shown in FIG. 5, the second emission path (from FIG. 4) is omitted while the second excitation source is maintained. In a single emission configuration (preferable for matters of reducing costs), the dual excitation cartridge 130 enables the measurement of fluorescence polarization without mechanically moving polarization filters thereby saving valuable measurement time, as described in the following paragraph.

According to the embodiment shown in FIG. 5, the apparatus 12 has a first light source 18 which produces a first exciting light 20 and a second light source 116 which produces a second exciting light 118. The apparatus 12 additionally has a power source 44 and the cartridge 130 has a coupler 46 for providing a current supply to light sources 18 and 116 from the power source 44. The dual excitation cartridge 130 has a first optical system 120, as described with respect to FIG. 4, which has components, including a first excitation filter 122 and a second excitation filter 124, for directing the first and second exciting lights 20 and 118, respectively, to a polarizing beam splitter 132. The polarized light beam 134 is directed to a sample 16 via reflector 26 and read head 28. The read head 28 directs the exciting light 134 toward the sample 16. The dual excitation measurement may be performed quasi simultaneously, by alternating the polarization state of the beam, i.e., electronically switching between the first and second light sources 18 and 116. The sample 16, containing the target 14, produces an emitting light 32. The dual excitation cartridge 130 has a second optical system 34, as described with respect to FIG. 1B, which receives the emitted light 32 from the read head 28 and directs the emitted light 32 from the sample to the detector 36. The emitted light 32, received from the read head 28 is transmitted through a reflector 26 by a mirror 48 towards the cartridge exit 40, which interfaces with the detector 36. Before exiting the cartridge 130, the emitted light 32 is filtered through a filter 42 which is sandwiched with a polarization analyzing sheet 136. According to this embodiment, the G-Factor is determined using an assay standard.

According to another embodiment of the invention shown in FIG. 5, the dual excitation cartridge 130 may be used for a new type of microplate assay technology which uses two light sources in combination for photoactivation of a sample by one light source, followed preferably by a fluorescence measurement using the other light source. According to this embodiment, a first exciting light (e.g., exciting light 118 from light source 116) and a second exciting light (e.g., exciting light 20 from light source 18) are directed to the target 14 in succession, i.e., one after the other. The target 14 contains or is associated with a functional group having an inactivated state and an activated state, e.g. "caged" functional groups of biochemical starter reagents which are activated by flash photolysis. The first exciting light 118 is first directed to the target 14 to change the functional group associated with the target 14 from the inactivated state to the activated state (i.e., the functional group associated with the target 14 is photoactivated). The photoactivation of the functional group is followed by a fluorescence measurement which is accomplished by directing the second exciting light 20 to the target 14 associated with the functional group, which is in the activated state, to produce an emitting light 32 in response to the second exciting light 20. The second optical system 34 receives the emitting light 32 produced by the functional group on the target 14 and directs the emitting light 32 from the target 14 to the detector 36.

The above cartridge system used for photoactivation is described with respect to analyzing the target 14 in the sample 16 by a single emission fluorescence measurement. However, as will be understood by those of skill in the art by reference to this disclosure, the invention is not limited by the above described example, and other embodiments of the cartridge system employing a cartridge that is capable of photoactivating a target in a first step and reading an emission from the activated target in a second step are envisioned. For example, other fluorescence measurement configurations may be used according to the present invention, such as dual emission fluorescence (described with respect to FIG. 4, for example). Alternately, the target 14 in the sample 16 may be analyzed with other optical measurements such as absorbance or luminescence. For example, the target 14 in the sample 16 may be measured using absorbance. According to this embodiment, the cartridge has a dual light source, the first light source being used to activate the functional group on the target 14, as described with respect to FIG. 5, but the cartridge and apparatus are reconfigured for absorbance detection. In another example, the target 14 in the sample 16 may be measured using luminescence. According to this embodiment, the second light source in the cartridge is omitted and the first light source is used as an activating light source to activate the functional group on the target 14, as described with respect to FIG. 5, but the cartridge and apparatus are configured for luminescence detection.

The cartridge system used for photoactivation of a sample has several advantages over other analogous systems that employ reagent injection technology such as (i) photoactivation does not involve reagent injection, which imposes some risk of instrument contamination due to aerosol build up, splashes onto optics, and/or leakage; (ii) photoactivation does not require mixing of injected reagents, which can have incomplete mixing, and a lack of reproducibility; (iii) caged starter reagents may be brought right into living cells in order to trigger a reaction within a cell by external optical means. Such reactions cannot be triggered by the physical injection of starter reagents into the sample which contains such cells.

Figure 6A:
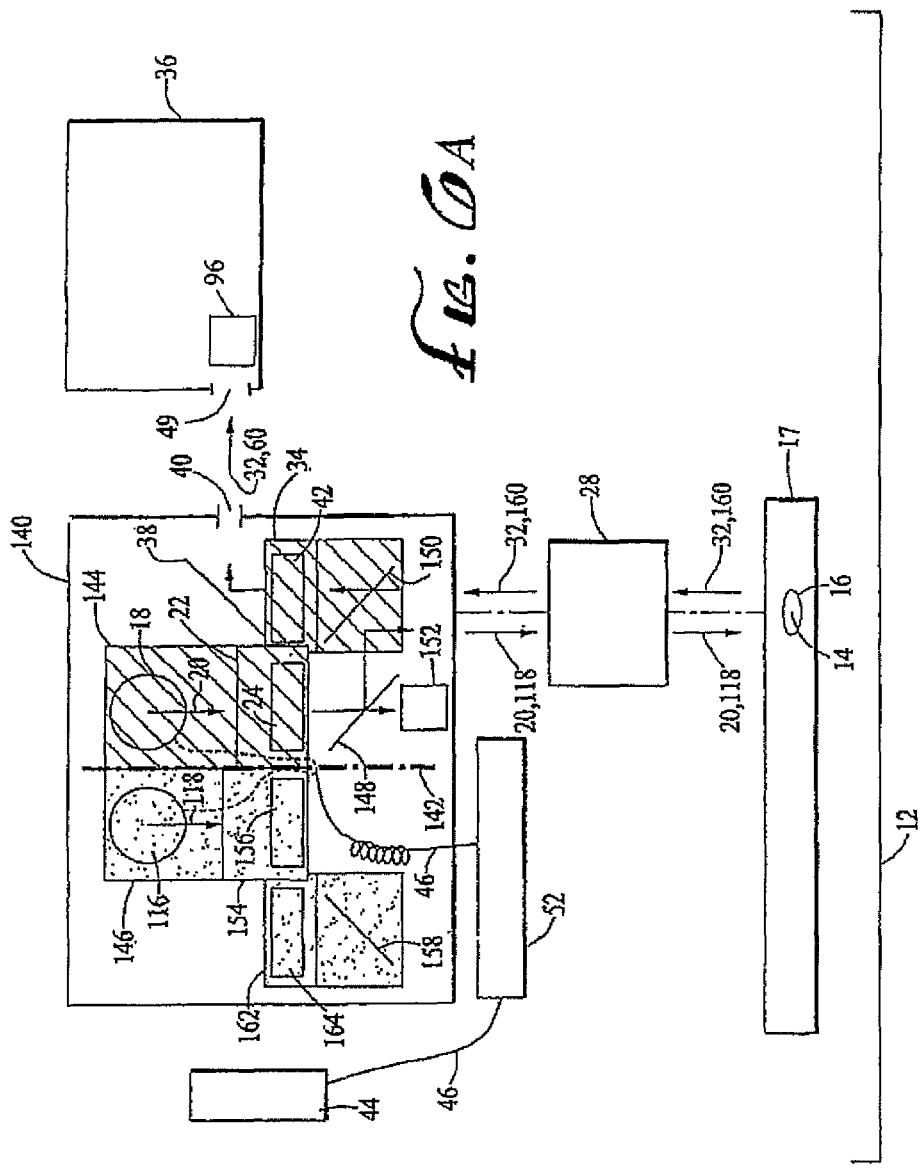
FIGS. 6A and 6B are schematic views of a multi-purpose cartridge, having multiple applications mounted on a revolver mechanism within the cartridge, according to an embodiment of the present invention.
Figure 6B:
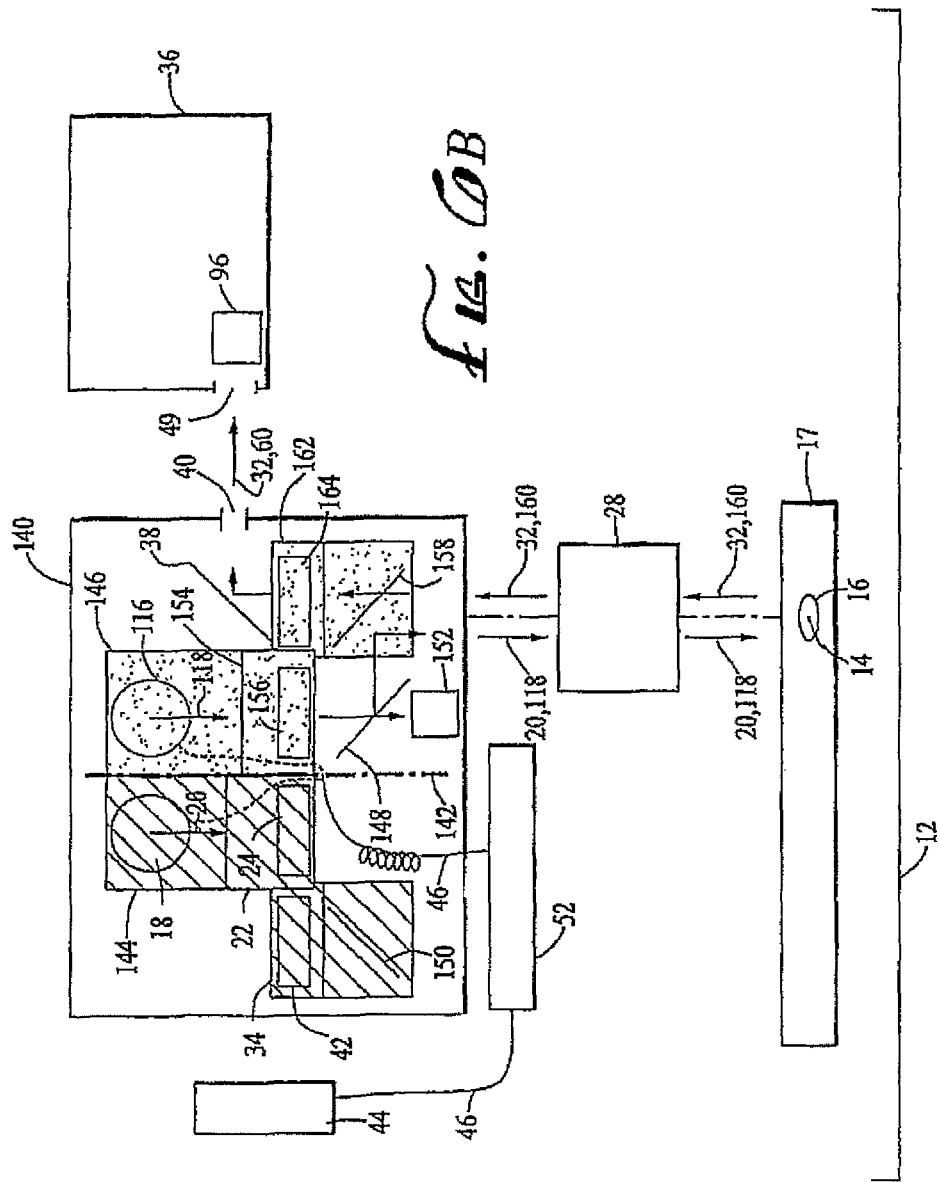

Referring now to FIG. 6A and FIG. 6B, another embodiment of the apparatus 12 for analyzing a target 14 in a sample 16 is shown. As shown in FIG. 6A and FIG. 6B, the apparatus 12 has a multi-purpose cartridge 140 that is equipped with multiple sections, or chambers, each section being configured for a particular spectroscopic application. The multi-purpose cartridge 140 may be equipped with multiple sections (e.g., 5 or 6), each chamber having an application specific set of light sources and/or optical systems that correspond to a particular application. In an alternative embodiment, a section (i.e., chamber, or section of the support) may be configured without a light source to provide a luminescence channel, i.e., luminescence light collected by the read head 28 is forwarded through a section of the cartridge 140 to the detector 36.

According to the embodiment shown in FIGS. 6A and 6B, the multi-purpose cartridge 140 has multiple light sources, each within a separate section, such as the first and second light sources 18 and 116, which are housed in first and second sections 144 and 146, respectively, as shown in FIGS. 6A and 6B. The multi-purpose cartridge 140 utilizes a revolver mechanism 142 that mounts each of the multiple sections, each section having an application specific set of optical systems, which correspond to the light source within a particular section e.g., each section houses excitation and emission filters, and a beam splitter for each different light source. The apparatus 12 additionally has a power source 44 and the multi-purpose cartridge 140 has a coupler 46 for providing a current supply to the multiple sections and light sources, such as light sources 18 and 116, from the power source 44 and is designed to be removably engaged with apparatus 12. According to the embodiment shown in FIGS. 6A and 6B, the power source 44 is coupled to light sources 18 and 116 by the coupler 46, as described with respect to FIGS. 1B and 1C. Inside the cartridge 140, between the cartridge plug and the light source control board 68 (shown in FIG. 2), the coupling continues with the help of a flat cable that coils up or uncoils again while the support 142 rotates.

As shown in FIGS. 6A and 6B, the multi-purpose cartridge 140 has a movable support 142 (e.g., a revolver-type mechanism), which mounts the first light source 18 and corresponding optics onto a first section 144 (i.e., a chamber) of the cartridge 140. The movable support 142 also mounts the second light source 116 and corresponding optics onto a second section 146 of the cartridge 140. The movable support 142 also mounts other sections e.g., sections 3, 4, 5, or more (not shown) onto the cartridge 140. A particular application provided by the first section 144 or second section 146, or other sections of the cartridge 140, (e.g., a particular wavelength of exciting light, as determined by the light source 18 or 116, or optical system for a luminescence application) is selected by moving the desired light source 18 or 116 into an operating position within the cartridge 140, e.g., by rotating a revolver mechanism of the movable support 142 about the axis (dotted line). FIG. 6A shows the operating position for the first light source 18 and FIG. 6B shows the operating position for the second light source 116.

Referring again to FIG. 6A, the first section 144 of the multi-color cartridge 140 comprises a first light source 18, which produces a first exciting light 20 (preferably collimated), and a first optical system 22, which has components, including a first excitation filter 24, for directing the first exciting light 20 to a partially reflecting mirror 148 and then to a dichroic beamsplitter 150 toward the read head 28. Prior to passing through the dichroic beamsplitter 150, a portion of the first exciting light 20 passes the partially reflecting mirror 148 and is measured by a detector 152, such as a photodiode, as previously described with respect to FIG. 2. The first exciting light 20 is directed to a sample 16 via a read head 28. The sample 16, containing the target 14, produces an emitting light 32. The first section 144 of the cartridge 140 has a second optical system 34, which receives the emitting light 32 from the read head 28 and directs the emitting light 32 from the sample 16 to the detector 36 via a filter 42, and a reflector 38, through the cartridge exit 40, which interfaces with the detector 36.

Referring again to FIG. 6B, the second section 146 of the multi-color cartridge 140 comprises a second light source 116, which produces a second exciting light 118 (preferably collimated), and a third optical system 154, which has components, including a first excitation filter 156, for directing the second exciting light 118 to a partially reflecting mirror 148 and then to the dichroic beamsplitter 158, and toward the read head 28. Prior to passing through the dichroic beamsplitter 158, a portion of the second exciting light 118 passes the partially reflecting mirror 148 and is measured by the detector 152, as previously described with respect to FIG. 2. The second exciting light 118 is directed to a sample 16 via a read head 28. The sample 16, containing the target 14, produces a second emitting light 160. The second section 146 of the cartridge 140 also has a fourth optical system 162, which receives the second emitting light 160 from the read head 28 and directs the second emitting light 160 from the sample 16 to the detector 36 via a filter 164, and the reflector 38, through the cartridge exit 40, which interfaces with the detector 36.

Referring now to FIG. 7, another embodiment of the apparatus 12 for analyzing a target 14 in a sample 16 is shown. According to the embodiment shown in FIG. 7, the apparatus 12 has a dual wavelength absorbance cartridge 170 that is equipped with first and second light sources 18 and 116, respectively. The apparatus 12 additionally has a power source 44 and the dual wavelength absorbance cartridge 170 has a coupler 46 for providing a current supply to light sources 18 and 116 from the power source 44. The dual wavelength absorbance cartridge 170 is designed to be removably engaged with apparatus 12.

As shown in FIG. 7, the dual wavelength absorbance cartridge 170 comprises first light source 18, which produces a first exciting light 20 (preferably collimated), and a first optical system 22, which has components, including a first excitation filter 24, for directing the first exciting light to a beam combiner 172 and then toward the sample 16. For absorbance applications, the beam is collimated to a smaller diameter than for fluorescence applications, and the excitation filters typically feature a smaller bandpass (i.e., narrower). For dual wavelength measurements, the dual wavelength absorbance cartridge 170 comprises a second light source 116, which produces a second exciting light 118, which is passed through a filter 124 and is aligned with the first exciting light 20 with help of the beam combiner 172 to produce a combined exciting light beam 174. The combined exciting light beam 174 is then passed through the cartridge support 52, via an aperture 176 (i.e., a window or light transparent section of the cartridge support 52) and focused into the sample 16, which is positioned on the sample support 17, via aperture 58. The dual wavelength measurement may be performed quasi simultaneously, by alternating the color of the combined beam 174, i.e., electronic switching between the first and second light sources 18 and 116. Emitting light 32 transmitted through the sample is collected by a read head 28 and focused onto an absorbance detector 178, containing, for example, a photodiode 38. Preferably, the signal measured at the photodiode 38 of the absorbance detector 178 is normalized with the beam intensity measured without the sample support 17. The signal is also normalized with respect to the light source monitoring circuitry, such as that described with respect to FIG. 2.

Figure 8:
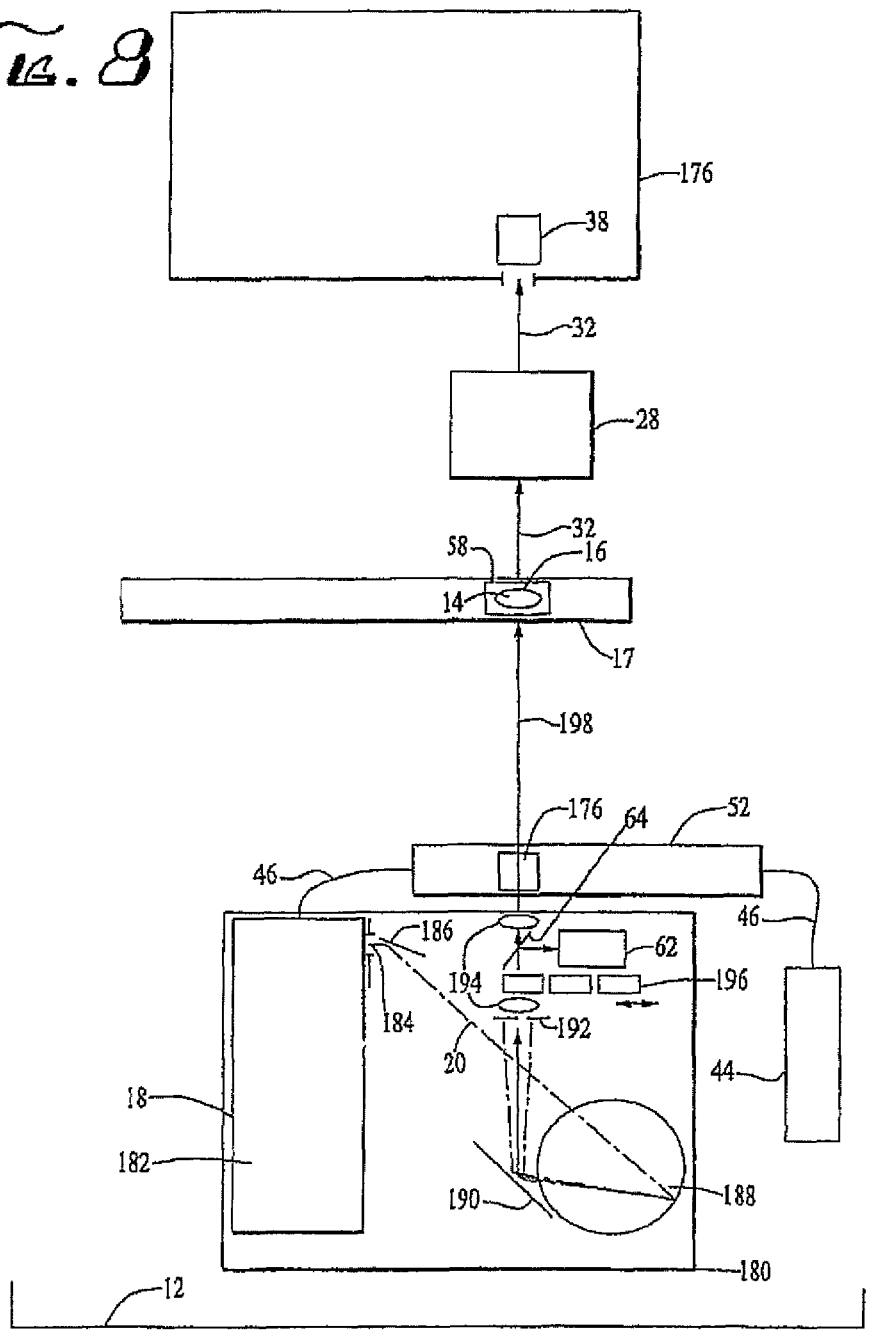
FIG. 8 is a schematic view of a wide band light source cartridge with wavelength selection according to an embodiment of the present invention.

Referring now to FIG. 8, another embodiment of the apparatus 12 for analyzing a target 14 in a sample 16 is shown. According to the embodiment shown in FIG. 8, the apparatus 12 has a wide band light source cartridge 180 that is equipped with a first light source 18, which preferably is a wide band light source 182, such as a Xenon flash lamp module. The apparatus 12 additionally has a power source 44 and the wide band light source cartridge 180 has a coupler 46 for providing a current supply to light source 18 from the power source 44. The wide band light source cartridge 180 is designed to be removably engaged with apparatus 12.

The wide band light source 182 is a light source that can provide an exciting light over a wide band of the Ultraviolet (UV), visible (VIS), and near infrared (NIR) electromagnetic spectrum, (i.e., light having a wavelength from about 200 nm to about 1000 nm). Preferably, a Xenon flash lamp module is used as the wide band light source 182 because of the high intensity over the desired wavelength operating range. The flash mode is selected for its lower heat dissipation when compared with a constant Xenon Arc Discharge lamp.

According to the embodiment shown in FIG. 8, the wide band light source cartridge 180 comprises a first light source 18 includes a wide band light source 182. The wide band light source 182 produces an exciting light 20, which exits slit 184 of the wide band light source 182 and is directed (via a reflector 186) onto a wavelength selector 188, such as a monochromator grating that disperses the exciting light 20 (different wavelengths into different angles). A mirror 190 maps the different angles (wavelengths) onto different positions across the monochromator's exit slit 192, shown as a fan of rays indicated by dotted lines in FIG. 8. The wavelength of exciting light 198 (non dotted line) transmitted through the slit 192 is selected by rotating the wavelength selector 188. Further functions housed in the cartridge 180 are beam shaping optics 194, order sorting filters 196 (to remove unwanted contamination of the desired beam wavelength with light from other than first order grating diffraction), sitting on a filter wheel, and a partially reflecting mirror 64 and photodiode 62 for monitoring the intensity of the exiting beam, such as described with respect to FIG. 2. After exiting the wide band light source cartridge 180, the combined exciting light beam 198 is passed through the cartridge support 52 via aperture 176 and then focused onto the sample 16, which is positioned on the sample support 17, via aperture 58. Emitting light 32 transmitted through the sample 16 is collected by a read head 28 and focused onto an absorbance detector 178, such as a photodiode 38. Preferably, the signal measured at the photodiode 38 of the absorbance detector 178 is normalized with the beam intensity measured without the sample support 17. The signal is also normalized with respect to the light source monitoring circuitry, such as that described with respect to FIG. 2.

According to the present invention, any of the above described cartridges having an exciting light source, such as the cartridges shown in FIGS. 3-8 may be controlled by the electronic measurement circuitry 68 and corresponding detector 62, apparatus controller 74, and feedback loops 66 and 72 described with respect to FIG. 2.

Figure 9:
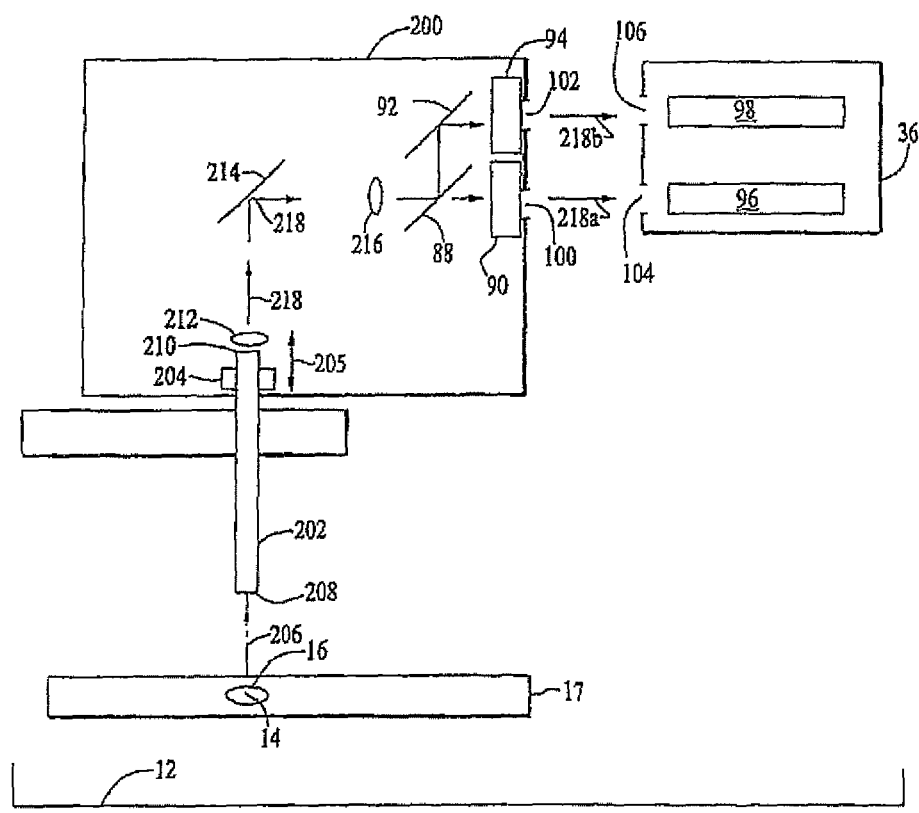
FIG. 9 is a schematic view of a luminescence cartridge, having an integrated read head, according to an embodiment of the present invention.

Referring now to FIG. 9, a luminescence cartridge 200 for use in an apparatus 12 for analyzing a target 14 in a sample 16 is shown. As shown in FIG. 9, the cartridge 200 comprises an integrated read head 202 and a driver 204, which moves the read head 202 in the direction indicated by arrow 205 into a detection position above the sample 16 when receiving emitting luminescent light 206 from the sample 16. The integrated read head 202 can also be moved by the driver 204 away from the sample 16 into a latent position when the luminescence cartridge 200 is not in use, or the apparatus 12 is being loaded with a new sample support 17. Preferably, the read head 202 is fully retractable into the cartridge 200, and also preferably, for reasons of saving measurement time, the read head 202 will not move up and down when moving from the one sample 16 to the next, but will stay in proximity above the sample support 17, when moving from one sample 16 to the next sample. The integrated read head 202 is retracted when the sample support 17 is moved in or out of the apparatus 12 in order to avoid parts of the sample support carrier (not shown) that extend beyond the upper sample support level.

Preferably, the integrated read head 202 is a rigid light guide that receives emitting luminescent light 206 at a proximal end 208 of the integrated read head 202 from a position above the sample holder 17 and sample 16. The emitting luminescent light 206 then exits the integrated read head 202 at a distal end 210 of the integrated read head 202 and is collimated by a lens 212 to produce a collimated light beam 218.

According to the embodiment of the luminescence cartridge 200 shown in FIG. 9, the apparatus 12 and luminescence cartridge 200 are configured for a bioluminescence resonance energy transfer (BRET) type measurement, where luminescence light is composed of two wavelength bands (e.g., a dual emission cartridge configuration) which is detected simultaneously with a dual channel detector. The dual emission cartridge and dual channel detector are further described with respect to FIGS. 3 and 4. As shown in FIG. 9, the collimated emitting luminescent light beam 218 is redirected with a reflector 214 toward a dichroic beamsplitter 88 via a lens 216 and separated into two wavelength bands 218a and 218b. The first wavelength band 218a is passed or transmitted by a beamsplitter 88 toward the detector 36 via a first emission filter 90 (e.g., a bandpass filter). The second wavelength band 218b is reflected by the beamsplitter 88, and reflected at the mirror 92 toward the detector 36 via a second emission filter 94 (e.g., a bandpass filter). The detector 36 is preferably a dual channel detector having two detectors 96 and 98 (e.g., photomultiplier tubes) stacked to form the dual channel detector. In addition, the luminescence cartridge 200 has a dual exit port 100 and 102, which is aligned with the detectors 96 and 98 via detector ports 104 and 106.

In an alternative embodiment, for a wider class of luminescence measurements, which do not require simultaneous measurement of two wavelength bands, the cartridge 200 may be simplified by omitting the beamsplitter 88, mirror 92, and second emission filter 94.

Referring now to FIG. 10, another embodiment of the invention, a cartridge system 220 for use in an apparatus 12 for analyzing a target in a sample (not shown) is provided. As shown in FIG. 10, the apparatus 12 has a cartridge support 232 (i.e., a slide mechanism or cartridge slider) which is configured to concurrently receive a multitude of different cartridges. According to this embodiment, a cartridge for a desired application, such as fluorescence, absorbance, or luminescence, is selected by the user and is selectively aligned by the apparatus 12 with the read head 28 and the detector 36 by moving the selected cartridge into the analysis position A, along the direction indicated by arrow 234. In this manner, a single instrument may house several application cartridges at a time and an application may be selected by the user without the user performing a multitude of application specific adjustments to the instrument such as selecting the correct combination and adjustment of filters, beamsplitters, apertures, and lightguides, etc. for a given application.

Referring again to FIG. 10, the cartridge system 220 comprises a plurality of cartridges, each cartridge being removably engaged with the apparatus 12. Examples of cartridges that may be used in the cartridge system 220 are one or more of the cartridges described in FIGS. 1-9. Exemplary cartridges used in the cartridge system 220 are shown in FIG. 10 as cartridge 222, cartridge 224, cartridge 226, cartridge 228, and cartridge 230. However, a greater or fewer number of cartridges may be used in the cartridge system 220 and the cartridges need not have the same dimensions such that cartridges having more complex systems (and larger dimensions) or less complex systems (and smaller dimensions) may be used in the apparatus 12. The apparatus 12 has a cartridge support 232 (i.e., a slide mechanism or cartridge slider) which is configured to receive the cartridges (e.g., cartridges 222, 224, 226, 228, and 230) and align each of the cartridges with the detector 36 and read head 28.

In a preferred but not required embodiment, each cartridge has indicia, such as an electrically erasable programmable read-only memory, EEPROM, that indicates the type of detection that the cartridge can be used for and the corresponding parameters for the particular cartridge. Also preferably, the cartridge support 232 features a cartridge detector, such as a data line function, or an electronic bus system, that enables the instrument control software (not shown) to identify a cartridge's slot position (i.e., the position of the cartridge on the cartridge support 232) and recognize any application specific parameters stored in the cartridge's EEPROM.

In another preferred but not required embodiment, the cartridge support 232 dimensions are such that it can be moved through a front door or access panel of the apparatus housing and every cartridge position or "slot" on the cartridge support 232 can be accessed for installation or removal of a cartridge. More preferably, one cartridge is capable of being removed from the cartridge support 232 and exchanged with a second cartridge, or alternately, a new cartridge is installed in an empty slot on the cartridge support 232 without the use of mechanical tools, or with a simple mechanical tool, such as for releasing a fastening mechanism (e.g., a fastening clip).

In another preferred but not required embodiment, at least one of the cartridges in the cartridge system 220 has one or more light sources that produces an exciting light, such as the cartridges described with respect to FIGS. 1-8. In another preferred but not required embodiment, at least one of the cartridges in the cartridge system 220 has an integrated read head and a driver (not shown), such as that described with respect to FIG. 9 for moving the read head. In some embodiments, at least one of the cartridges in the cartridge system 220 is a wavelength-tunable cartridge 10, 80 or 110 such as those described above and illustrated in FIGS. 1D, 1E, 3A and 4A.

Figure 11:
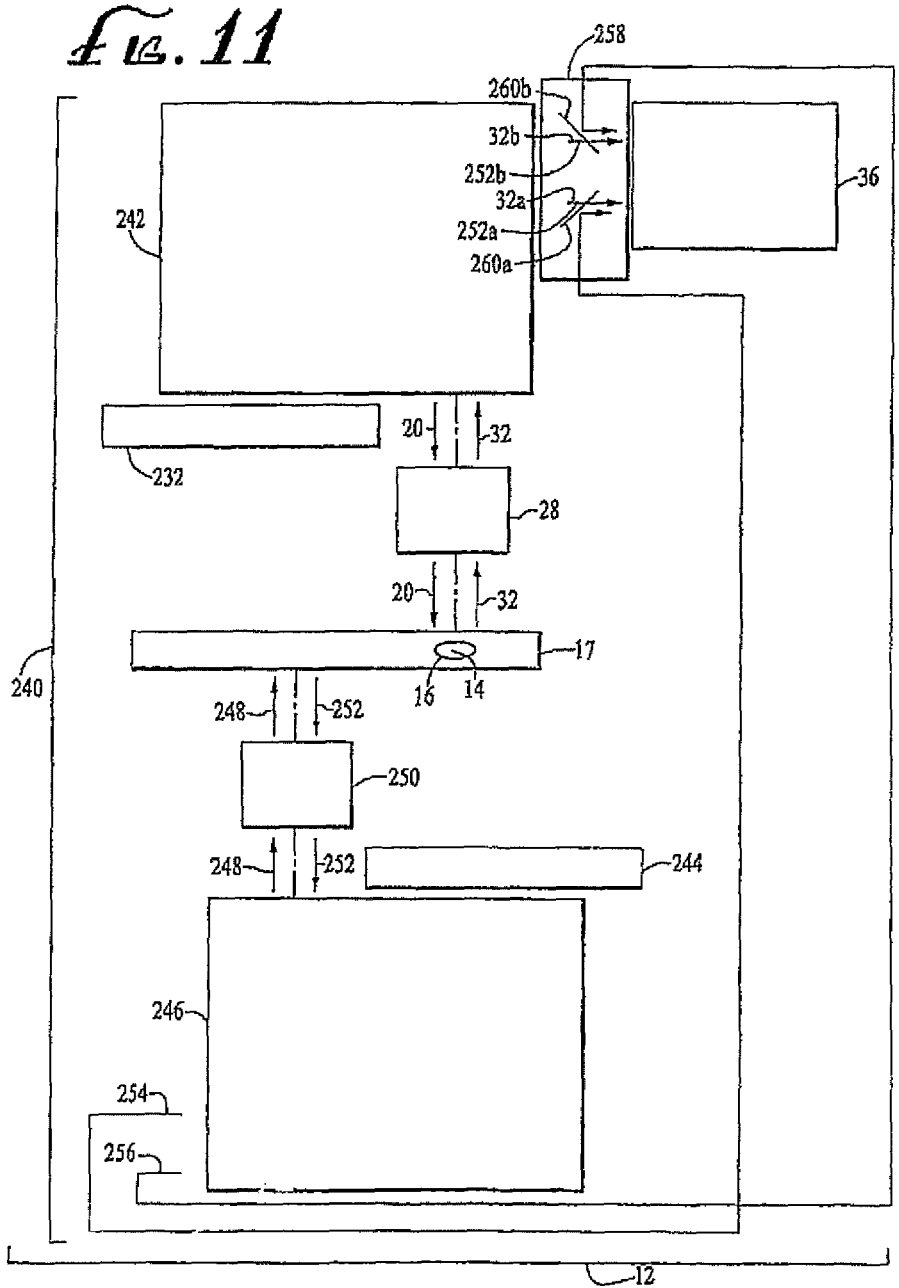
FIG. 11 is a schematic view of a top and bottom reading cartridge system according to an embodiment of the present invention.

Referring now to FIG. 11, another embodiment of the invention, a top and bottom reading cartridge system 240 for use in an apparatus 12 for analyzing a target 14 in a sample 16 is provided. As shown in FIG. 11, the apparatus 12 has a first cartridge support 232 which supports a first cartridge 242 and a second cartridge support 244 which supports a second cartridge 246. The first and second cartridges 242 and 246 may be any of those described herein such as the cartridges described with respect to FIGS. 1-9, but preferably are configured for fluorescence applications. As noted above in the description relating to FIGS. 1B and 1C, the first cartridge support 232 and/or the second cartridge support 244 may be configured for supporting a plurality of cartridges, and for selectively aligning one or more of the cartridges with the read head 28 or 250 and/or the detector 36, as appropriate for carrying out a particular type of measurement.

According to the embodiment shown in FIG. 11, the first cartridge support 232 and first cartridge 242 are positioned above the sample support 17. The exciting light 20 from the first cartridge 242 is directed to the sample 16 through a first read head 28. The emitting light 32 from the sample 16 is then directed again through the first cartridge 242, by which the emitting light 32 is directed to the detector 36 as previously described herein, for example, with respect to FIGS. 1-6. The emitting light 32 may be split into one or more wavelength bands 32a and 32b as previously described. The second cartridge support 244 and second cartridge 246 are positioned below the sample support 17 and the exciting light 248 from the second cartridge 246 is directed to the sample 16 through a second read head 250. The emitting light 252 is then directed again through the second cartridge 246, where it is split into emitting lights 252a and 252b and relayed remotely to the detector 36. Preferably, light guides 254 and 256 relay the emitting light 252a and 252b from the bottom of the second cartridge 246 through an exit port (not shown) to the detector 36.

In some embodiments, a wavelength-tunable cartridge 10, 80 or 110, such as those described above and illustrated in FIGS. 1D, 1E, 3A and 4A, is loaded at the first cartridge support 232 and thus above the sample support 17 for top reading, or is loaded at the second cartridge support 244 and thus below the sample support 17 for bottom reading, or two wavelength-tunable cartridge 10, 80 or 110 may be respectively loaded at the first cartridge support 232 and the second cartridge support 244. When loaded at the second cartridge support 244, the wavelength-tunable cartridge 10, 80 or 110 may optically communicate with the output detector 36 positioned above the sample support 17 via one or more light guides 254, 256 such as optical fibers.

The design of the first and second cartridges 242 and 246 is independent of whether the cartridge is positioned either above or below the sample support 17. However, when the cartridge configuration shown in FIG. 11 is used, a movable detector port support 258 (e.g., a slide or selector wheel mechanism) is used which switches the detector 36 from seeing either emitting light 32a and 32b from the first cartridge 242 and first read head 28 or seeing emitting light 252a and 252b from the second cartridge 246 and second read head 250. The emitting light 252a and 252b exiting the light guides 254 and 256 is reflected into the detector 36 by mirrors 260a and 260b. The selection between the first and second cartridges 242 and 246 is done by moving the movable detector port support 258 along an axis 262 perpendicular to the detector 36. This embodiment is further detailed in FIG. 12.

Figure 12:
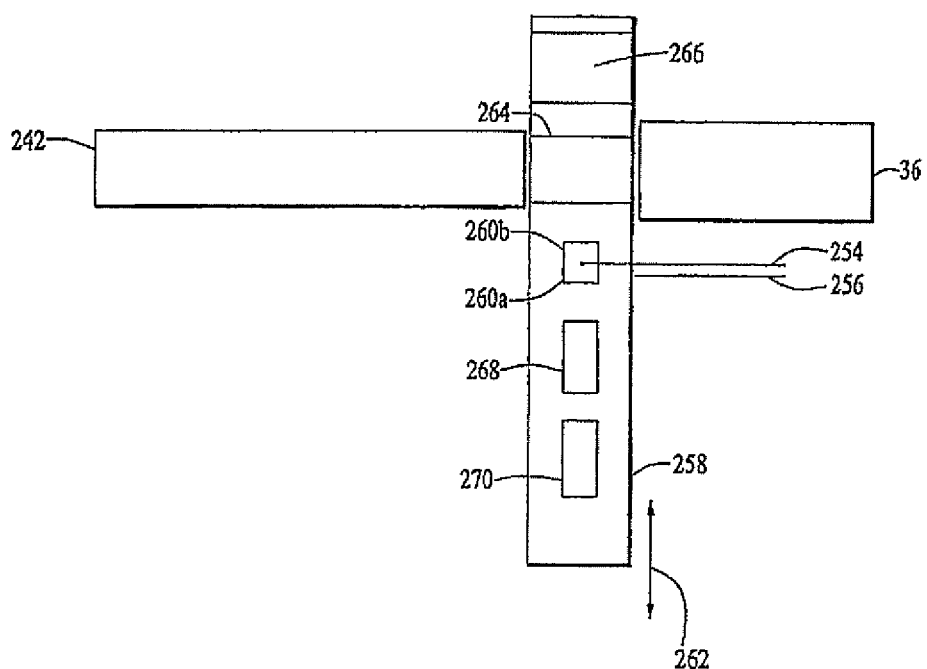
FIG. 12 is a schematic top view of the cartridge configuration shown in FIG. 11.

According to the embodiment shown in FIG. 12, the movable detector port support 258 is located in the gap between the exit of the first cartridge 242 and the entrance to the detector 36. The movable detector port support 258 houses an aperture 264 (e.g., a beam pass) which directs emitting light 32a and 32b from the first cartridge 242 and a beam stop/shutter 266 which protects the detector 36 when the instrument front door is opened, such as for maintenance or to exchange a cartridge. The movable detector port support 258 may also be equipped with light attenuating filters 268 and 270 which enable the system to analyze a signal that is too strong for the detector 36. The movable detector port support 258 may also be equipped with a constant low power light source in order to monitor the function and performance of the detector 36 over longer periods of operation (not shown). The light source resident in the detector port support 258 is built from a LED and stabilized by feedback from a photodiode, as described for a cartridge with respect to FIG. 2. The LED output is attenuated down to levels acceptable to the detector 36 by help of a diffusing glass. Another position along the movable detector port support 258 may house mirrors 260a and 260b that reflect the emitting light 252a and 252b exiting the light guides 256 and 254 from above and below the movable detector port support 258. Emitting light 252a and 252b exiting the light guides 256 and 254 can enter the detector 36 when the position of the light guides 256 and 254 on the detector port support 258 is aligned with the detector 36.

As is evident from FIGS. 2 and 8, in certain embodiments a removable cartridge may include a detector. As is also evident from FIGS. 1C, 7, 8 and 11, in certain embodiments systems implementing absorbance measurements such as illustrated in FIGS. 1C, 7 and 8 may be adapted to the top and bottom cartridge configuration illustrated in FIG. 11. As examples, the absorbance cartridge 10 shown in FIG. 1C, the dual wavelength absorbance cartridge 170 shown in FIG. 7, or the wide band light source absorbance cartridge shown in FIG. 8 may be loaded onto the second (bottom) cartridge support 244 shown in FIG. 11. In a further example, the absorbance detector 178 shown in FIGS. 7 and 8 may be provided in a removable cartridge that is loaded onto the first (upper) cartridge support 242 shown in FIG. 11. In such embodiments, the sample support 17, first cartridge support 242 and/or second cartridge support 244 may include apertures 58, 176 (FIGS. 7 and 8) as needed, and one or both read heads 28 and 250 may be bypassed as needed.

Figure 13:
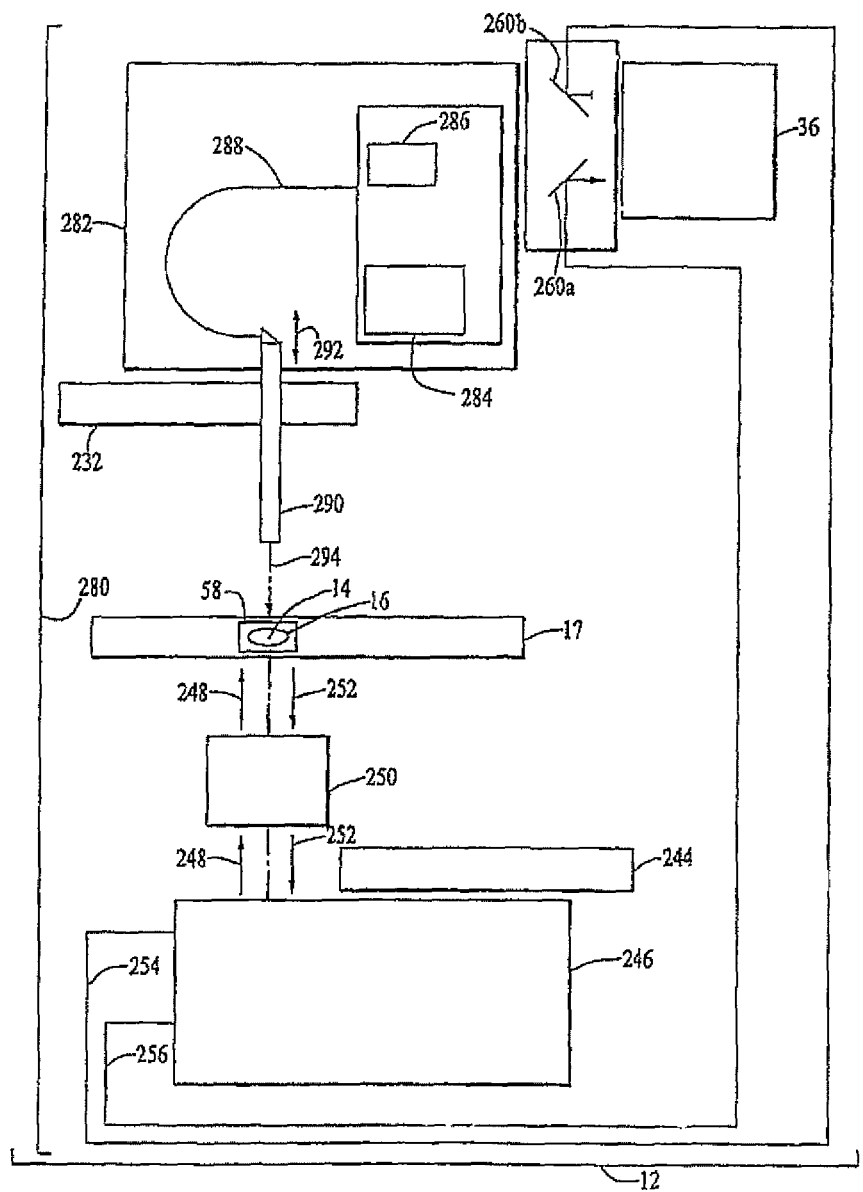
FIG. 13 is a schematic view of a flash fluorescence cartridge system according to an embodiment of the present invention.

Referring now to FIG. 13, another embodiment of the invention, a flash fluorescence cartridge system 280 for use in an apparatus 12 for analyzing a target 14 in a sample 16 is provided. The flash fluorescence cartridge system 280 has an injector cartridge (i.e., the first cartridge 282) that may be used for flash fluorescence applications, which require injection of a starter reagent in combination with immediate fluorescence reading.

For typical flash fluorescence applications, clear bottom microplates are frequently used as the sample support 17 (i.e., a sample support having an aperture 58) such that injection of the reagent occurs from above the well and fluorescence is measured simultaneously from below the sample holder 17. Accordingly, FIG. 13 uses the top and bottom reading cartridge configuration, which has been described with respect to FIG. 11. According to the embodiment shown in FIG. 13, an injector cartridge 282 is installed as the first cartridge (i.e., the upper cartridge) on the first cartridge support 232. A second cartridge 246 is positioned on a second cartridge support 244. The second cartridge 246 may be any of those described herein such as the cartridges described with respect to FIGS. 1-6 and 13, but configured for a fluorescence application. As noted again, the first cartridge support 232 and/or the second cartridge support 244 may be configured for supporting a plurality of cartridges, and for selectively aligning one or more of the cartridges with the read head 250 and/or the detector 36, as appropriate for carrying out a particular type of measurement.

As shown in FIG. 13, the first cartridge 282 features a reagent reservoir 284, a pump 286, and a tubing system 288 connected to a nozzle 290 (preferably rigid). The nozzle 290 can be driven down from within the first cartridge 282 to approach the sample support 17 from above, as shown by arrow 292. The nozzle 290 is aligned with a sample 16 and read head 250 and reagent 294 is delivered to the sample 16 via the nozzle 290. Exciting light 248 and emitting light 252 is directed to the sample 16 and subsequently to the detector 36 as described with respect to FIG. 11. Sample measurement may take place before, during, and after injection of reagent 294.

Using an injector module that can be easily removed under routine operating conditions, such as the injector cartridge described herein, provides several advantages. The injector cartridge and external docking station may also be used as a precision dispenser apparatus. In addition, the cartridge's tubing system can be easily rinsed/cleaned by the customer and primed, i.e., floated, thereby removing bubbles, with the reagent outside of the instrument enclosure. This may occur with the injector cartridge still plugged into the cartridge support, but with the cartridge support moved through the instrument door and having a waste reservoir placed underneath. Priming may also occur with the injector cartridge removed from the cartridge support and plugged into a docking station. Both strategies reduce the risk of accidentally floating the interior of the apparatus with reagent. Also, the output of the injector cartridge can be calibrated for the customer's solvents at the customer site using an external docking station mounted on top of weighing scales.

Referring now to FIG. 14, another embodiment of the invention, a flash luminescence cartridge system 300, for use in an apparatus 12 for analyzing a target in a sample (not shown) is provided. Measurement of flash type luminescence requires the injection of a starter reagent, and measurement of luminescence light at a fraction of a second later. The configuration of the cartridge system 300 for this application has an injector cartridge 282, as described with respect to FIG. 13 and a luminescence cartridge 200 as described with respect to FIG. 9. The injector cartridge 282 and the luminescence cartridge 200 are positioned on adjacent slots on the cartridge support 232 as described with respect to FIG. 10. Any combination of cartridges may be possible (see for example FIG. 6). However, the cartridges are typically dedicated to a single (or only few) applications, unless the required performance would not be compromised by including an additional application. Preferably, due to the proximity of the injection position and the read position, the luminescence cartridge 200 and the injector cartridge 282 are fused into a single, dual slot cartridge.

As shown in FIG. 14, the luminescence cartridge 200 is aligned with the detector 36 and detects emitting light 32 from a first target 14a (not shown) on the sample support 17, which is positioned below the cartridge support 232. A flash type luminescence measurement is performed by first aligning the luminescence cartridge 200 with the detector 36 in the analysis position indicated in FIG. 14. The cartridge support 232 is then in a fixed position until the sample analysis is complete. The sample support 17 is then moved to align the first sample 16a (not shown) with the injector cartridge 282 in a first position, i.e., an "injecting position," position A. Starter reagent is then injected onto the first sample 16a. After the starter reagent is injected, the sample support 17 is then moved such that the first sample 16a on the sample support 17 is in a second position i.e., a "reading position," position B, where the first sample 16a is aligned with the luminescence read head (not shown) within the luminescence cartridge 200. A measurement may be taken on a second sample 16b (not shown) by moving the sample support 17 to the injecting position, i.e., the "injecting position," position A, below the injector cartridge 282 and injecting starter reagent onto the second sample 16b. The sample support 17 is then moved such that the second sample 16b on the sample support 17 is in the second position i.e., the "reading position," position B, where the second sample 16b is aligned with the luminescence read head (not shown) within the luminescence cartridge 200.

Figure 15A:
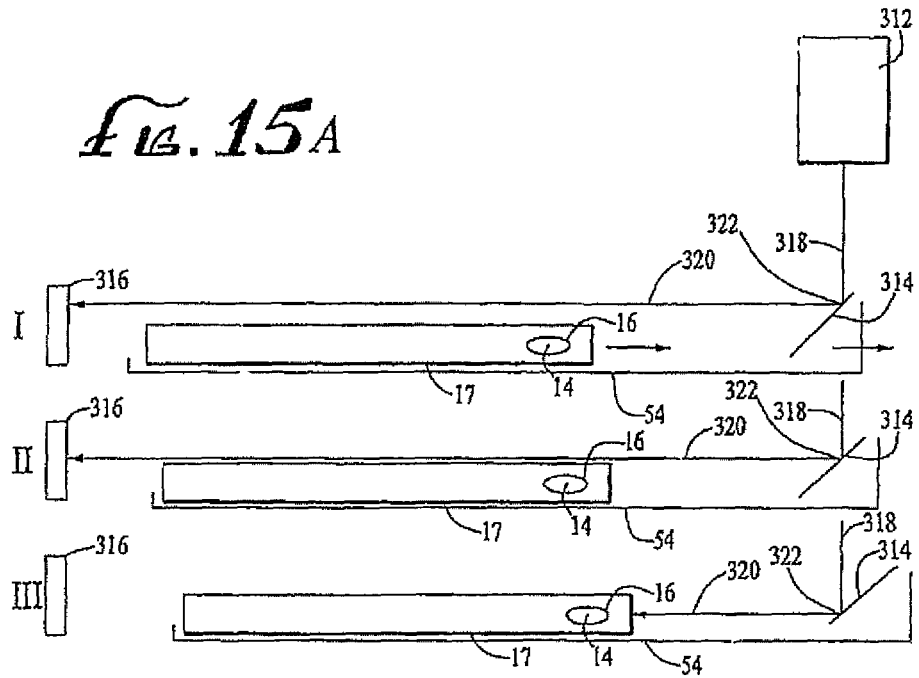
FIGS. 15A and 15B are schematic views of a system for detecting the sample support clearance in a cartridge according to an embodiment of the present invention.
Figure 15B:
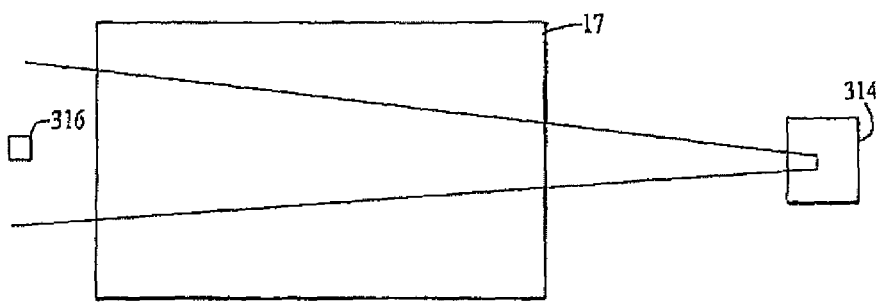

According to another preferred but not required embodiment of the invention, a sample support detector 310 for use in a system for analyzing a target 14 in sample 16 is shown in FIGS. 15A and 15B. As shown in FIG. 15A, a side view of the sample support detector 310, and FIG. 15B, a top view of the sample support detector 310, the sample support detector 310 comprises a detecting light source 312 (e.g., a laser pointer), a reflector 314 (e.g., a mirror) and a detector 316 (e.g., a photodiode). The sample support detector 310 measures the clearance (i.e., height) of the sample support 17 to avoid the luminescence read head or a fluorescence read head, which, when seeking to receive maximum signal from a sample may be moved down too far and thus collide with the top of the sample support 17. The result of the measurement produced by the sample support detector 310 is a value that instructs the software of the apparatus not to move lower than the particular value determined by the measurement.

According to the embodiment shown in FIGS. 15A and 15B, the detecting light source 312 produces a light beam 318, such as a laser line from a laser pointer, which is directed in the direction of the sample support 17. The reflector 314 is attached to the sample support carrier 54. Before reading the sample 16, the sample support carrier 54 is loaded with a sample 16 positioned on a sample support 17 outside the apparatus in a sample support loading position. To acquire a sample reading, the sample support carrier 54 must be retracted into the apparatus. On its way from the sample support loading position, outside the apparatus, to an inside initialization position, the sample support carrier 54 passes the detecting light source 312. Then, the light beam 318 is inflected (i.e., redirected) by the reflector 314 to produce an inflected light beam 320, which is parallel to the surface of the sample support 17, and then contacts the detector 316, as shown in FIG. 15A, view I. Then, the reflector 314 is moved such that the inflection point 322 of the light beam 318 on the reflector 314 moves down along the reflector surface until the inflected light beam 320 comes closer to the surface of the sample support 17, as shown in FIG. 15A, view II, and is further moved until the inflected light beam 318 is obstructed by the edge of the sample support 17, as shown in FIG. 15A, view III.

Preferably, as shown in FIG. 15A, the detecting light source 312 is positioned perpendicular to the sample support 17 and the reflector 314 redirects the light beam 318 at an angle of about 45 degrees so the inflected light beam 320 is approximately parallel to the sample support 17. Consequently, the signal at the photodiode undergoes an ON/OFF transition. By calibration using sample supports of different height, the position of the sample support 17 where the ON/OFF transition occurs is a measure of the height of the sample support 17.

As shown in FIG. 15B, alignment may be made less demanding by using a laser line pointer for the light beam 318 and projecting a fan of rays parallel to the surface of the sample support 17. The photodiode's sensitive area is extended in the direction orthogonal to the laser line projection (shown in FIG. 15B as vertical). Thereby, when not yet obstructed by the sample support 17, the fan of rays always has an intersection with the light detector 316.

Dynamic Signal Extension

Figure 16:
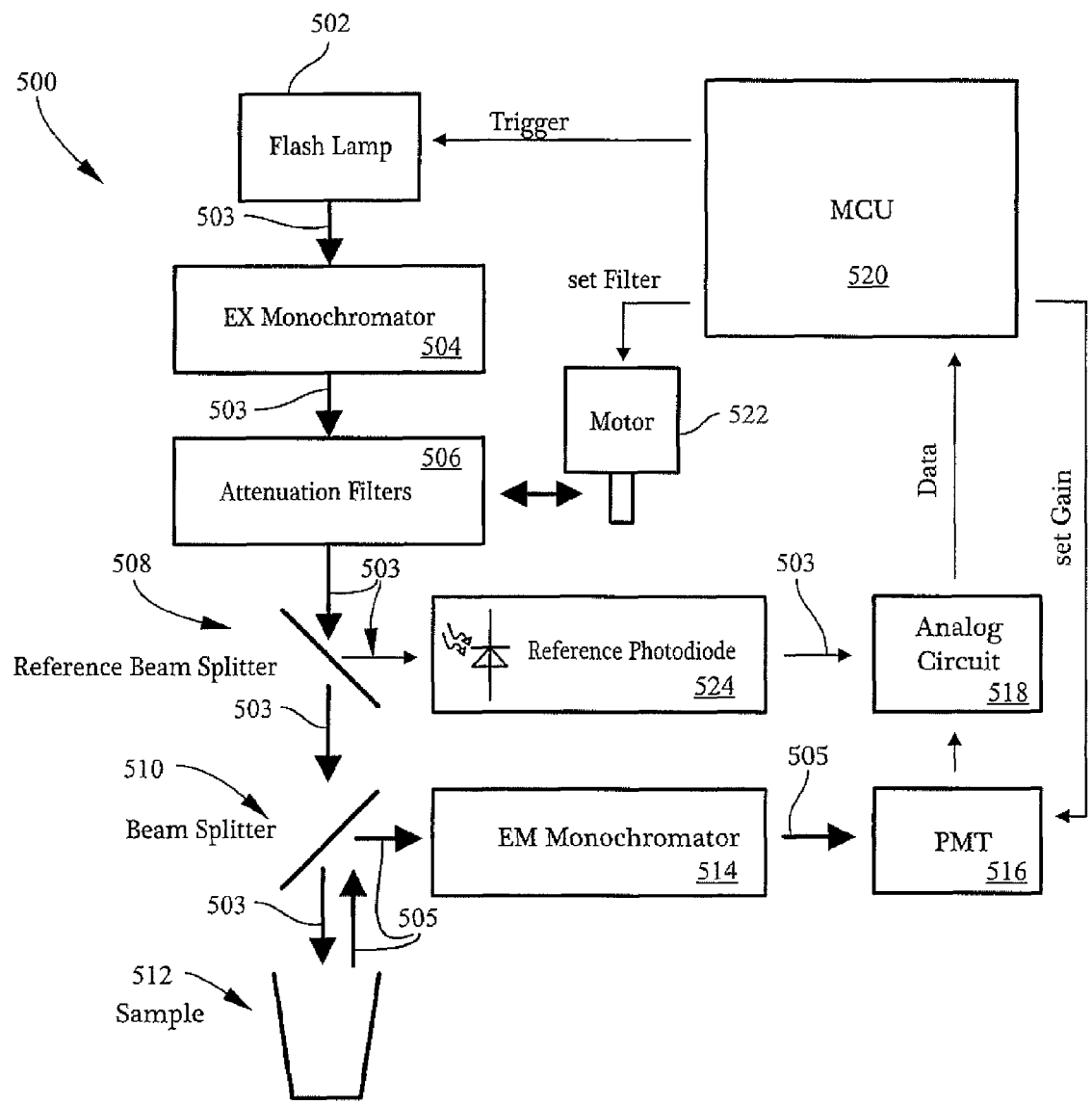
FIG. 16 is a block diagram of an example of a system for performing fluorescence measurements that employs dynamic signal extension.

As described above with reference to FIGS. 1-15B, cartridges may be configured to include different light sources, optical systems and other components to implement specific applications in an analytical instrument system. The cartridges reduce the extent to which new applications and technologies in a multimode reader system require redesign or retrofitting. Example implementations of an analytical instrument may include implementations of systems and methods for performing dynamic signal extension in fluorescence or absorbance signal measurements to expand the functionality of systems that support combined filter-based and monochromator-based technologies. FIG. 16 is a block diagram of an example of a system 500 for performing dynamic signal extension in a measurement system that uses a light energy detector. The system 500 in FIG. 16 may be used particularly in applications that perform fluorescence measurement using a PMT 516 as the light energy detector.

The system 500 includes an excitation light source, which is implemented as a flash lamp 502 in the example shown in FIG. 16, an excitation monochromator 504, and an attenuation filter arrangement 506. The flash lamp 502 is positioned to provide an excitation optical signal along an excitation optical path 503. The excitation monochromator 504 is positioned in the excitation optical path 503 and controlled to pass a selected wavelength of the excitation light. The excitation monochromator 504 in FIG. 16 may operate similarly to the components configured to select a wavelength in the exciting light 20 in the wide band light source cartridge 180 illustrated in FIG. 8. For example, the excitation monochromator 504 may include a grating positioned in the excitation optical path 503 to spectrally spread the excitation light. An optical component, such as a mirror or lens, may be positioned at the part of the spectrum of the excitation light that corresponds to a selected wavelength in order to extend the excitation optical path at the selected wavelength.

The excitation light exits the excitation monochromator 504 at the selected wavelength along the excitation optical path 503 to the attenuation filter arrangement 506. The attenuation filter arrangement 506 is controlled to select an attenuation filter to position in the excitation optical path 503. The attenuation filter arrangement 506 may include any selected number of attenuation filters having varying attenuation factors. A dynamic signal extension method may be performed by a software program executed by a controller 520 to select an appropriate attenuation filter that reduces the intensity of the emitted light from the sample 512 to within a signal output range of the PMT 516. In an example method, each reading of the PMT 516 is checked for an overflow. If any individual reading results in an overflow condition at the PMT 516, the attenuation filter arrangement 506 is controlled to provide a higher level of attenuation for a next reading.

The controller 520 may generate a control signal, indicated as a 'set filter' signal in FIG. 16, pursuant to the dynamic signal extension method to add attenuation to the excitation light when a PMT overflow is detected in a reading. The 'set filter' signal may be configured to drive a motor 522 to position a selected attenuation filter in the attenuation filter arrangement 506 in the excitation optical path 503. The motor 522 may be configured to drive an apparatus with the attenuation filters and a filter-less slot positioned serially so that the motor may move the selected attenuation filter (or filter-less slot) into the excitation optical path 503. The selected attenuation filter attenuates the excitation light in the excitation optical path 503 by a known factor. The excitation light exits the attenuation filter arrangement 506 and continues to a reference beam splitter 508.

The reference beam splitter 508 reflects a part of the excitation light from the excitation optical path 503 to a reference photodiode 524. The reference photodiode 524 generates a signal corresponding to a reference light intensity of the excitation optical path 503. An analog-to-digital converter circuit 518 generates a digital value corresponding to the reference light intensity of the excitation optical path 503. The controller 520 uses the reference light intensity to determine the intensity of the excitation light for each reading. If a reading is taken with an attenuation filter to attenuate the excitation light, the reference light intensity is used with a system reference level to correct the reading for the attenuation. The system reference level may be a constant scaling factor. In an example implementation, the system reference level may represent an un-attenuated excitation light level, or some maximum excitation light level. However, the system reference level may be set to any value so long as it is maintained a constant.

The attenuated excitation light is directed along the excitation optical path via a measurement beam splitter 510 to the sample 512, from which an emission light may be generated in response to receiving the excitation light. The measurement beam splitter 510 passes the excitation light to the sample 512 and reflects the emitted light from the sample 512 along an emission light path 505. The emitted light is received at an emission monochromator 514 in the emission light path 505. The emission monochromator 514 passes the emitted light at a selected wavelength to the PMT 516. The PMT 516, operating in analog mode, generates a measured signal level indicative of an emitted light level as measured by the PMT 516. The emitted light level may be for example an intensity level, and the measured signal level may be an analog electrical signal. The measured signal level output from the PMT 516 is passed to the analog-to-digital converter 518 to provide a digital value as data representing the measured signal level of the emitted light.

The PMT 516 may be characterized as having a maximum detector level, which may depend on the gain to which the PMT 516 is set. The maximum detector level of the PMT 516 is a maximum electrical signal level that the PMT 516 is capable of generating in response to an input light level. If a measured signal level is greater than the maximum detector level, an overflow condition may be indicated. The signal output of the PMT 516 may be read as part of a pre-measurement adjustment if an overflow, or excess signal, is detected for the PMT 516. As described in more detail with reference to FIG. 17 below, one of the attenuation filters in the attenuation filter arrangement 506 may be selected to adjust the optical path for the PMT 516. The adjustment is based on obtaining light energy at the exit of the excitation monochromator 504 that is not overly bright for the current gain setting of the PMT 516. When a reading does not result in an overflow, that reading is determined to be valid signal data for the sample.

In example implementations of the system 500 in FIG. 16, a method for reading signal level from a PMT for a sample in analog mode may be performed where the method self-adjusts when the signal range for a given application exceeds the range of the PMT without changing the gain of the PMT 516. A PMT gain may be selected for the PMT 516 for measurements to be taken from the sample 512 based on the requirements of a particular application. For the selected PMT gain, the measurement signal output of the PMT 516 has a range. In some applications, the light level emitted by a sample may drive the PMT 516 to generate an output signal that correlates to a light level that would be above the signal range of the PMT 516. In this case, the measurement signal output of the PMT 516 would be at the maximum of the PMT output range and valid signal level may be cutoff. Adjusting the gain of the PMT 516 to expand the signal output range would take too much time to perform for individual measurements. In example implementations of the system 500, the attenuation filter arrangement 506 may be triggered to select an attenuation filter that adjusts the excitation light such that the range of the PMT 516 signal output covers a signal level for the sample provided by the PMT 516 responsive to the attenuated excitation light. The selection of a suitable attenuation filter may be performed much more rapidly than the resetting of the PMT gain. Example implementations of dynamic signal extension may be performed in a fraction of the normal measurement time for an individual sample in microplate. The measurements taken with attenuated excitation light may be corrected using the reference level and system reference level in order to generate results that can be compared with measurements taken with unattenuated excitation light, or with excitation light attenuated at different factors.

Figure 17:
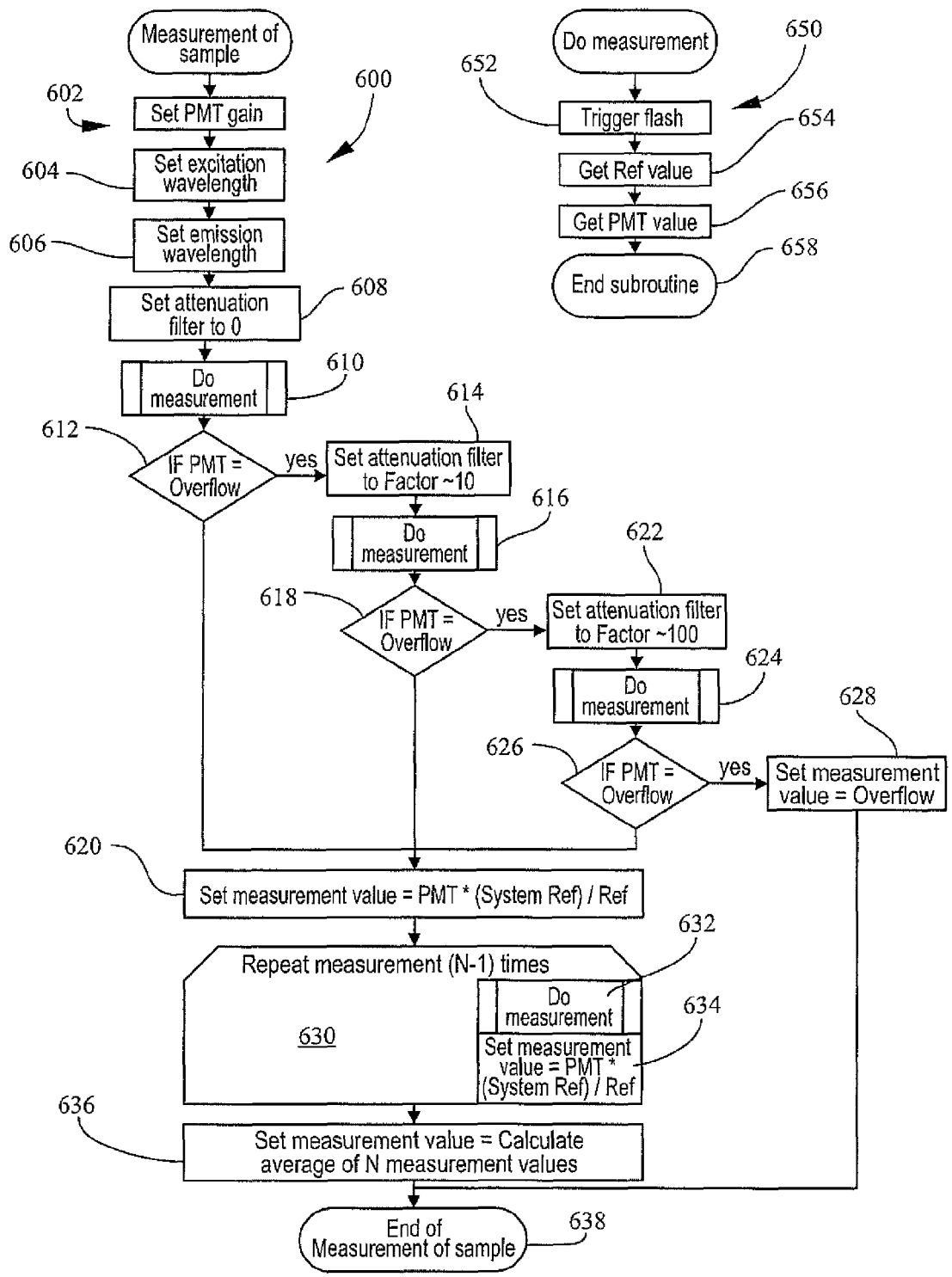
FIG. 17 is a flowchart illustrating operation of an example fluorescence measurement system that employs dynamic signal extension using the system shown in FIG. 16.

FIG. 17 is a flowchart illustrating operation of an example of dynamic signal extension in the system shown in FIG. 16. The flowchart in FIG. 17 illustrates operation of methods that may be performed using the system 500 in FIG. 16. In example implementations, functions for performing dynamic signal extension methods may be computer programmed functions executed by the controller 520 in FIG. 16.

FIG. 17 includes a flowchart for a signal measurement function 600 incorporating dynamic signal extension if needed using attenuation filters to generate a measurement of the emission light from the sample. The signal measurement function 600 is performed with a sample at a particular well on a microplate, for example, to generate sample reading data. The signal measurement function 600 in FIG. 17 may be implemented to obtain sample reading data for multiple samples in a multi-sample holder, such as a microplate. By performing dynamic signal extension, sample readings may be conducted in a single scan of the microplate with the PMT 516 set at a constant gain. FIG. 17 also includes a flowchart for a raw signal measurement function 650 that includes obtaining a reading from the reference photodiode 524.

At step 602 of the signal measurement function 600, the PMT 516 may be programmed to operate at a specific gain according to the application for which signal measurements are to be taken. The gain of the PMT 516 may be set using a "set gain" control signal generated by the controller 520 in accordance with the operation of the PMT 516. At step 604, the excitation monochromator 504 may be preset to pass the excitation light at a selected wavelength. The excitation monochromator 504 may be controlled in a manner similar to that described above with reference to FIG. 8. At step 606, the emission monochromator 608 may be preset to pass the emission light at a selected wavelength. At step 608, the controller 520 issues a 'set filter' control signal to preset the attenuation filter arrangement 506 with no attenuation filter inserted into the excitation light path 503. The excitation light path 503 will pass un-attenuated during the measurement to the reference beam splitter 508.

At step 610, a measurement is performed using the raw signal measurement function 650 in FIG. 17. At step 652 of the raw signal measurement function 650, the controller 520 triggers the flash lamp 502 to generate a signal, which may be of a duration of a few microseconds. At step 654, a reference value is read from the reference photodiode 504 (for example, as shown in FIG. 16), which represents the excitation light intensity. At step 656, a PMT value is read from the PMT 516 in FIG. 17. The PMT value that is read represents the signal measurement for a particular sample being tested.

At decision block 612, the signal measurement read from the PMT at step 656 of the raw signal measurement function 650 is analyzed to determine if there was an 'overflow' of the PMT 516. The 'overflow' may be indicated by a flag generated by the PMT 516 and read by the controller 520. The value of the signal measurement indicating an overflow may also be generated by the PMT 516. An 'overflow' is indicated when the measurement signal value returned is too high for the PMT 516 at the current gain setting. If decision block 612 determines that the measurement signal generates an overflow condition at the PMT 516, a 'YES' path is taken and the attenuation filter arrangement 506 is set to enable a first attenuation filter at step 614. In an example implementation, the first attenuation filter may be designated as having a factor ~10. The factor ~10 attenuation filter may be a suitable ~1 OD ("optical density") filter, which reduces the light energy level to ~10% of the maximum energy light output.

With the ~1 OD attenuation filter now in the excitation light optical path, another signal measurement is performed using the raw signal measurement function 650, at step 616. At decision block 618, the signal measurement reading and the PMT 516 are checked for an overflow. If another overflow is indicated, a 'YES' path is taken from decision block 618 and the attenuation filter arrangement 506 is set to enable a second attenuation filter at step 622. In an example implementation, the second attenuation filter may be designated as having a factor ~100. The second attenuation filter may be implemented using a suitable ~2 OD filter, which reduces the light energy level to ~1% of the maximum energy light output.

With the ~2 OD attenuation filter now in the excitation light path, another signal measurement is performed using the raw signal measurement function 650, at step 624. At decision block 626, the signal measurement reading and the PMT 516 are checked for an overflow. If another overflow is indicated, a 'YES' path is taken from decision block 626 and at step 628, the measurement value is set to a value indicative of 'Overflow.' Since overflow is indicated with the ~1 OD filter and the ~2 OD filter, and no other filters are available in this implementation, the setting of the measurement value to the 'Overflow' value is an error condition. The method 600 then ends at step 638 and the controller 520 performs functions that may be corrective, or informative (annunciating an error). A corrective action may include for example, using another gain setting for the PMT and executing the dynamic signal extension method 600 again with a different gain setting. Other types of corrective action may be indicated in accordance with the specific application being performed.

It is noted that the example illustrated in FIG. 17 performs the method 600 using an attenuation filter arrangement 600 with only three settings: 1) no attenuation, 2) 90% attenuation, and 3) 99% attenuation. In other implementations, more or fewer attenuator filters may be used to provide additional settings for attenuation.

Referring to FIG. 17, if no PMT overflow is detected at decision blocks 612, 618, and 626, a correction is performed to generate a corrected sample measurement value, $S_1$=PMT_signal_output*(System Ref)/Ref, where PMT_signal_output is the digital value representing the PMT measurement signal output. At step 630, the measurement of the signal at the PMT output is performed an additional N−1 times. In particular, step 630 performs the raw signal measurement function 650, and the measured PMT signal output is used to calculate another value $S_N$=PMT_signal_output(N)*(System Ref)/Ref, where PMT_signal_output(N) is the digital value representing the PMT measurement signal output for the Nth measurement performed. At step 630, a set of N corrected sample measurement values, $S=\{S_1, S_2, S_3, \ldots, S_N\}$ is generated. At step 636, an average sample measurement value, $S_{AVE}$, is determined as $S_{AVE}$=AVERAGE(S). The method ends at step 638 with presentation of a resulting signal level as the data reading for the sample being measured.

The example system for performing a fluorescence measurement illustrated in FIG. 16, and the example method described in FIG. 17, advantageously permit a fluorescence measurement system to use a PMT in analog mode in monochromator-based implementations. It is noted that the system and method in FIGS. 16 and 17 are presented in the context of a multimode reader. However, the systems and methods described in FIGS. 16 and 17 may be advantageously implemented in single mode reader instruments as well. Similar implementations may be used in systems that make absorbance measurements to advantageously extend signal range in systems that implement analog-to-digital electronics that may not take full advantage of the range of the photodiode used for absorbance measurements.

Figure 18:
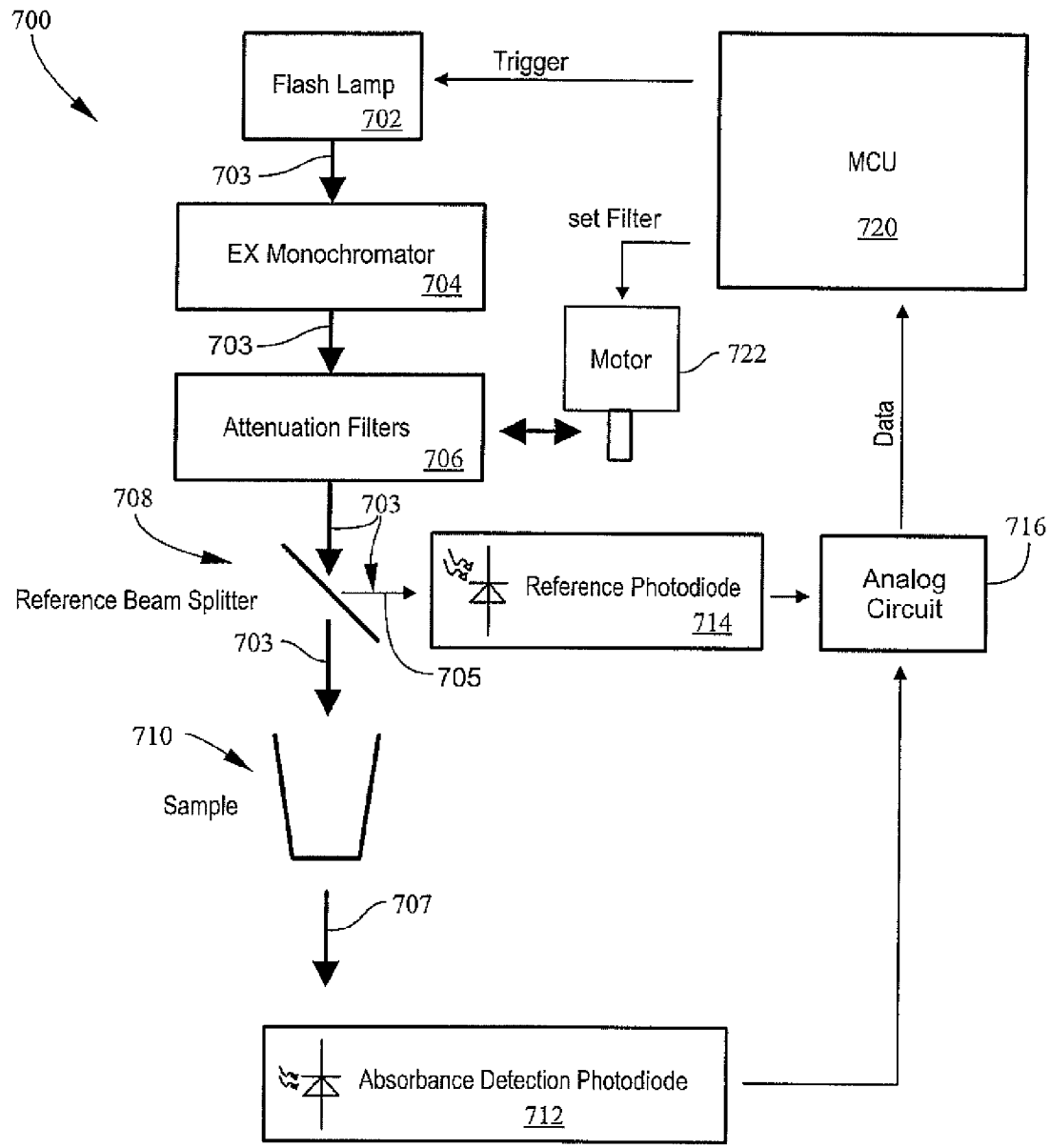
FIG. 18 is a block diagram of an example of a system for performing absorbance measurements that employs dynamic signal extension.

FIG. 18 is a block diagram of an example of a system 700 for performing dynamic signal extension in a measurement system that uses a photodiode 712 as the light energy detector. The system 700 in FIG. 18 includes a flash lamp 702 as the excitation light source, an excitation monochromator 704, and an attenuation filter arrangement 706, each of which may be the same or similar to the arrangement illustrated in FIG. 16. In some example implementations, a common flash lamp, monochromator, and attenuation filter filters arrangement may be provided for both fluorescence and absorbance measurements in a multimode reader environment. In other implementations, the systems 600 in FIG. 16 and 700 in FIG. 8 may be implemented in cartridges as described above.

A controller 720 triggers the flash lamp 702 to generate a flash or burst of light creating an excitation light that follows an excitation optical path 703. The excitation optical path 703 passes through the excitation monochromator 704, which passes the excitation light at a selected wavelength. The excitation optical path 706 then proceeds to the attenuation filters arrangement 706, which may or may not set an attenuation filter in the excitation optical path 703 for dynamic signal extension. The excitation optical path 703 passes to a reference beam splitter 708, which reflects some of the excitation light along a reference optical path 705 towards a reference photodiode 714. The reference photodiode 714 measures an intensity of the portion of the excitation light on the reference optical path 705 and determines a reference excitation light level. The reference excitation light level is converted by an analog-to-digital converter circuit 716 to a digital data value indicating the intensity of the portion of the excitation light on the reference signal path 704.

The reference beamsplitter 708 also passes the excitation light to a sample 710, which absorbs an amount of the excitation light and passes a transmitted signal 707 to an absorbance detection photodiode 712. The absorbance detection photodiode 712 measures the level of the transmitted signal 707 and communicates the analog level to the analog-to-digital converter circuit 716. The digital value representing the sample signal reading is then communicated to the controller 720.

Figure 19:
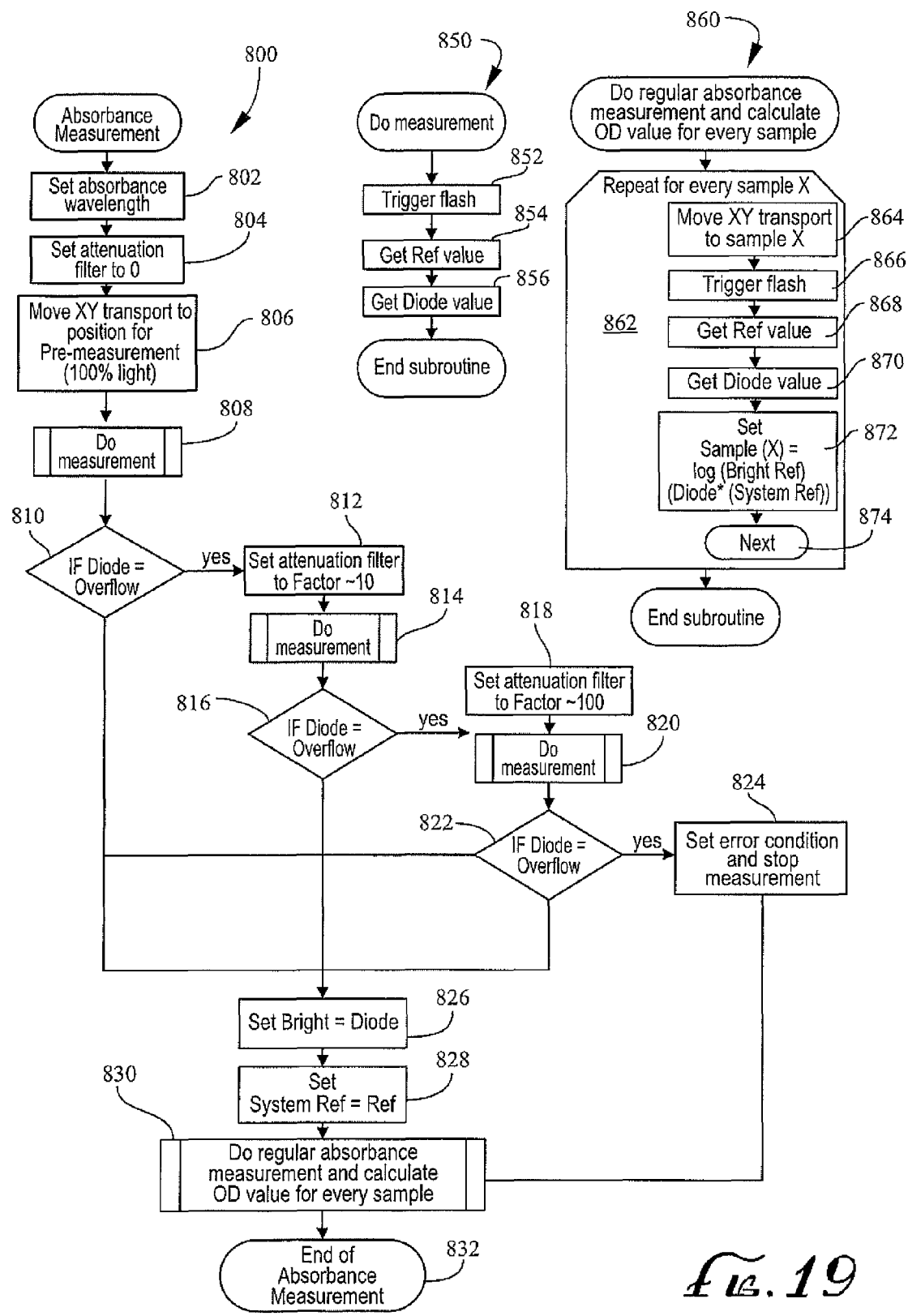
FIG. 19 is a flowchart illustrating operation of an example absorbance measurement system that employs dynamic signal extension using the system shown in FIG. 18.

In example implementations of the system 700 in FIG. 18, methods for obtaining a sample reading may be performed so that they include dynamic signal extension methods such as example methods illustrated in FIG. 19. In implementation, the methods illustrated in FIG. 19 may be invoked by the absorbance measurement system 700 (in FIG. 18) for example, when samples (in a microplate, for example) are ready for reading. For purposes of illustrating operation of the methods shown in FIG. 19, the methods are to be understood as being performed in the context of absorbance measurements of samples in a microplate. Either the reader apparatus (including the absorbance detection photodiode 712) or the microplate may move along an x-y plane.

FIG. 19 includes three flowcharts illustrating operation of an example absorbance measurement system that employs dynamic signal extension using the system shown in FIG. 18. The first flowchart in FIG. 19 illustrates operation of a signal measurement function incorporating dynamic signal extension 800. A pre-measurement is performed as described below to select an attenuation filter. The pre-measurement is followed by a reading of multiple samples in the microplate. In the example described below, there are X samples to be measured.

FIG. 19 also illustrates operation of a raw signal measurement function 850, and of an absorbance sample reading 860. The raw measurement method 850 includes the steps for an absorbance reading starting with triggering the flash lamp. The absorbance sample reading method 860 is performed to obtain absorbance readings of up to X samples that will be the data from which analysis of the samples is performed. The absorbance sample reading method 860 makes use of the reference readings taken during the signal measurement function incorporating dynamic signal extension 800.

Prior to performing the signal measurement function incorporating dynamic signal extension 800, the samples in the wells of a microplate have undergone any sample preparation and/or processing necessary per the application, and are ready to be read. The sample reading begins by performing the signal measurement function incorporating dynamic signal extension 800, which may be invoked in an application system by the controller 720. At step 802, an absorbance wavelength is selected by presetting the excitation monochromator 704 (for example). The wavelength selected is the wavelength of the excitation light from the flash lamp 702 that exits the excitation monochromator 704 along the excitation optical path 703. At step 804, the attenuation filters arrangement 706 is set to provide an attenuation of 0. The excitation light, when generated, would exit the attenuation filters arrangement 706 and continue towards the reference beam splitter 708.

At step 806, the microplate is moved so that the reader mechanism including the absorbance detection photodiode 712 is positioned to take a reading of a maximum signal, or a signal representing 100% light. The microplate is moved completely away from the excitation optical path to enable an absorbance reading for air. The air absorbance reading is then stored as a 'System Ref' value.

At step 808, a measurement is performed using the raw signal measurement function 850 in FIG. 19. At step 852 of the raw signal measurement function 850, the controller 720 triggers the flash lamp 702 to generate an excitation light, which lasts for a duration of a few microseconds. At step 854, a reference value is read from the reference photodiode 714 (for example, as shown in FIG. 18), which represents the excitation light intensity. At step 856, an absorbance reading is taken from the absorbance detection photodiode 712 and stored as a 'DIODE' value. For an absorbance reading at step 808, the 'DIODE' value represents the maximum (100% light) value with no attenuation of the excitation light.

At decision block 810, the 'DIODE' value is checked to determine if an overflow condition exists. Overflow in the context of absorbance measurements is similar to 'overflow' in the context of readings from a PMT. The overflow condition may be indicated by a value that represents a maximum possible value for the photodiode even though some amount of valid signal is not reflected in the 'DIODE' value. For example, the photodiode signals may be converted to digital using an A/D converter that generates samples with a number of bits that may not be sufficient for the valid signal range of the photodiode, or may not be sufficient at a desired resolution. If an overflow condition is indicated at decision block 810, the 'YES' path of decision block 810 is followed to step 812 at which the attenuation filters arrangement 706 is adjusted to select an attenuation filter with Factor ~10. With the Factor ~10 filter in position to attenuate the optical signal, another absorbance measurement is performed at step 814 to generate a new 'DIODE' value. The new 'DIODE' value is checked for overflow at decision block 816. If overflow is indicated again, the 'YES' path of decision block 816 is followed to step 818 at which the attenuation filters arrangement 706 is adjusted to select an attenuation filter with Factor ~100. With the Factor ~100 filter in position to attenuate the optical signal, another absorbance measurement is performed at step 820 to generate a new 'DIODE' value. The new 'DIODE' value is checked for overflow at decision block 822. If decision block 822 detects another overflow condition, the system generates an error condition at step 824.

If at decision blocks 810, 816, or 822, an overflow condition is NOT detected, the 'NO' path of the decision blocks lead to step 826 at which a 'BRIGHT' parameter is set to be equal to the 'DIODE' value as checked in the decision block that did not detect an overflow condition. At step 828, a 'SYSTEM REF' parameter is set to 'REF,' which is the signal read by the reference photodiode 714 during the raw signal measurement 850. At step 830, the absorbance measurement system then turns to detecting absorbance measurements for up to X samples in the microplate by performing the absorbance sample reading method 860.

In the absorbance sample reading method 860 at step 862, the positioning of the reader to each sample out of X samples, and the absorbance measurement is repeated for every sample. Step 862 includes steps 864, 866, 868, 870, 872, and 874. At step 862, the reader is positioned to the next sample x out of X, which is a selected first sample where x=1. At step 866, the controller 720 triggers the flash lamp on. At step 868, the value 'REF,' is read from the reference photodiode 714 for sample x. At step 870, the value 'DIODE,' is read from the absorbance detection photodiode 712 for sample x. At step 872, an absorbance reading value, S(x) is determined to be: S(x)=log(('BRIGHT'*REF$_x$)/('DIODE$_x$*System Ref)), where BRIGHT is the value read in for the absorbance photodiode when the absorbance of air, or 100% light, measurement was taken at step 808 without having to further attenuate the excitation light. At step 874, x=x+1 and the next sample is identified for measurement. Steps 864, 866, 868, 870, 872, and 874 are repeated for each sample x until x=X.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A system for measuring a target in a sample, the target being capable of generating an emitted light in response to an excitation light, the system comprising:

an excitation light source configured to generate the excitation light along an excitation optical path;

an attenuation filter arrangement configured to selectively add an attenuation filter to the excitation optical path to attenuate the excitation light by a corresponding attenuation factor, where the excitation light exits the attenuation filter arrangement along the excitation optical path to illuminate the sample;

an emission monochromator disposed to receive the emitted light generated by the target in the sample in response to the excitation light, the emission monochromator configured to output the emitted light at a selected wavelength;

a photomultiplier tube (PMT) disposed to receive the emitted light from the emission monochromator, the PMT configured to measure an emitted light level and to output a measured signal level up to a maximum detector level;

a reference photodiode configured to measure a reference excitation light in the excitation optical path indicative of an excitation light level of the excitation light exiting the attenuation filter arrangement;

a reference beam splitter configured to reflect a part of the excitation light exiting the attenuation filter arrangement to the reference photodiode; and a controller configured to:

receive the measured signal level and to execute a signal measurement function under program control, the signal measurement function configured to control the attenuation filter arrangement to add the attenuation filter to attenuate the excitation light if the measured signal level indicates an overflow condition in which the measured signal level is greater than the maximum detector level, to receive another measured signal level in response to an attenuated excitation light, and to process the measured signal level as a sample measurement value when the measured signal level does not indicate an overflow condition; and correct the measured signal level by a factor of REF/SYSTEM REF, where:

REF=Reference excitation light level, and

SYSTEM REF=Maximum excitation light level.

2. The system of claim 1, where the attenuation filter arrangement includes a plurality of attenuation filters each having a corresponding attenuation factor, and where the signal measurement function is configured to control the attenuation filter arrangement to add a first attenuation filter to attenuate the excitation light when the excitation light level indicates the overflow condition without attenuation, and to subsequently add attenuation filters with increasing attenuation factors after each measured signal level in response to an attenuated excitation light indicating an overflow condition.

3. The system of claim 1, further comprising:
an excitation monochromator configured to receive the excitation light energy and emit the excitation light energy at a selected wavelength.

4. The system of claim 1, where the controller is configured to set the PMT to a gain that remains constant during acquisition of measured signal levels for the sample.

5. The system of claim 1, where the controller is configured to obtain N measured signal levels from the PMT, correct each of the N measured signal levels by the factor of REF/SYSTEM REF, and determine the sample measurement level as an average of the N measured signal levels.

6. The system of claim 1, where the attenuation filter arrangement comprises:
a first attenuation filter having an attenuation factor of ~10; and
a second attenuation filter having an attenuation factor of ~100;
where the first attenuation filter is selected to attenuate the excitation light if the excitation light with no attenuation results in the overflow condition, and the second attenuation filter is selected to attenuate the excitation light if the excitation light attenuated by the first attenuation filter results in the overflow condition.

7. A method for analyzing a target in a sample, the target being capable of generating an emitted light in response to an excitation light, the method comprising:
generating an excitation light along an excitation light path to illuminate the sample, and to generate an emitted light from the sample;
passing the emitted light from the sample through an emission monochromator, and outputting the emitted light at a selected wavelength from the emission monochromator to a photomultiplier tube (PMT);
at the PMT, detecting a measured signal level from the emitted light;
if the measured signal level indicates an overflow condition in which the measured signal level is greater than a maximum detector level, performing the steps of:
adding an attenuation filter having a corresponding attenuation factor to the excitation light path to attenuate the excitation light by operating an attenuation filter arrangement, where the excitation light exits the attenuation filter arrangement along the excitation optical path; and
detecting a measured signal level from the emitted light in response to the attenuated excitation light;
processing the measured signal level as a sample measurement value when the measured signal level does not indicate an overflow condition,
where each step of detecting the measured signal level further comprises:
detecting a reference excitation light level in the excitation optical path indicative of an excitation light level of the excitation light exiting the attenuation filter arrangement, by reflecting a part of the excitation light exiting the attenuation filter arrangement to a reference photodiode; and
correcting the measured signal level for each sample by a factor of REF/SYSTEM REF, where:
REF=reference excitation light level, and
SYSTEM REF=Maximum excitation light level.

8. The method of claim 7, further comprising:
before the step of detecting the measured signal level, setting a gain of the PMT.

9. The method of claim 7, where the attenuation filter is a first attenuation filter in an attenuation filter arrangement that includes a second attenuation filter, the method further comprising:
after the step of detecting a measured signal level from the emitted light in response to the attenuated excitation light, performing the steps of:
adding the second attenuation filter having a corresponding attenuation factor greater than the attenuation factor of the first attenuation filter to the excitation light path to further attenuate the excitation light; and
detecting a measured signal level from the emitted light in response to the further attenuated excitation light.

10. The method of claim 7, further comprising:
repeating the steps of detecting the measured signal level in response to the excitation light and detecting the measured signal level in response to the attenuated excitation light to generate N measured signal levels for the sample;
repeating the step of correcting the measured signal level to generate N corrected measured signal levels for the sample;
calculating an average of the N corrected measured signal levels to determine the sample measurement level.

11. The method of claim 7, further comprising the step of:
selecting a wavelength for the excitation light;
enabling a wavelength selector to receive the excitation light and to transmit the excitation light at the selected wavelength.

12. The method of claim 7, where the step of adding the attenuation filter comprises selecting a ~10 attenuation filter having an attenuation factor of ~10.

13. The method of claim 9, where the step of adding the second attenuation filter comprises selecting a ~100 attenuation filter having an attenuation factor of ~100.

* * * * *